(12) United States Patent
Grimoldby et al.

(10) Patent No.: US 10,512,729 B2
(45) Date of Patent: Dec. 24, 2019

(54) PRIMING ARRANGEMENT FOR DRUG DELIVERY DEVICE

(71) Applicant: Owen Mumford Limited, Oxfordshire (GB)

(72) Inventors: James Grimoldby, Oxfordshire (GB); Oliver Gareth Hyde, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 194 days.

(21) Appl. No.: 15/749,582

(22) PCT Filed: Aug. 19, 2016

(86) PCT No.: PCT/GB2016/052573
§ 371 (c)(1),
(2) Date: Feb. 1, 2018

(87) PCT Pub. No.: WO2017/029515
PCT Pub. Date: Feb. 23, 2017

(65) Prior Publication Data
US 2018/0221584 A1    Aug. 9, 2018

(30) Foreign Application Priority Data
Aug. 20, 2015   (GB) .................................. 1514827.3

(51) Int. Cl.
*A61M 5/32*    (2006.01)
*A61M 5/31*    (2006.01)
(Continued)

(52) U.S. Cl.
CPC ........ *A61M 5/3146* (2013.01); *A61M 5/2033* (2013.01); *A61M 5/31505* (2013.01);
(Continued)

(58) Field of Classification Search
CPC ........ A61M 2005/2411; A61M 5/3146; A61M 5/31511; A61M 5/3202; A61M 5/3204; A61M 5/3158; A61M 5/3272
See application file for complete search history.

(56) References Cited

U.S. PATENT DOCUMENTS

| | | | |
|---|---|---|---|
| 2010/0280461 A1 | 11/2010 | Forstreuter | |
| 2010/0286619 A1* | 11/2010 | Abry | A61M 5/2033 604/192 |
| 2017/0014578 A1* | 1/2017 | Bunch | A61M 5/3202 |

FOREIGN PATENT DOCUMENTS

| | | |
|---|---|---|
| EP | 2 886 144 A1 | 6/2015 |
| GB | 2516624 A | 2/2015 |

(Continued)

OTHER PUBLICATIONS

Jan. 11, 2017 International Search Report for PCT/GB2016/052573.
Jan. 11, 2017 Written Opinion of International Searching Authority for PCT/GB2016/052573.

*Primary Examiner* — Rebecca E Eisenberg
(74) *Attorney, Agent, or Firm* — Hahn Loeser & Parks LLP

(57) ABSTRACT

An injection device (100) for injection of a medicament from a pre-filled container (10) having a container body (12) for containing the medicament, a needle (16) disposed at a distal end of the container body (12), a removable needle shield (30) and a stopper (22) for expelling medicament from the container (100), the device comprising a housing (110) for housing the container (10), a plunger (142) for driving the stopper (22) of the container (10) in a distal direction to expel the medicament, and a priming mechanism having an operating member (152) which is movable with respect to the housing (110). The priming mechanism is arranged to release the needle shield (30) from the needle (16) and to move the container body (12) in a proximal (Continued)

direction with respect to the plunger (142) upon movement of the operating member (152) from a first position to a second position during an operating sequence of the device.

47 Claims, 13 Drawing Sheets

(51) Int. Cl.
*A61M 5/20* (2006.01)
*A61M 5/315* (2006.01)
*A61M 5/24* (2006.01)

(52) U.S. Cl.
CPC ...... *A61M 5/31511* (2013.01); *A61M 5/3202* (2013.01); *A61M 5/3204* (2013.01); *A61M 2005/2006* (2013.01); *A61M 2005/2411* (2013.01)

(56) References Cited

FOREIGN PATENT DOCUMENTS

| | | |
|---|---|---|
| WO | WO 2007/099044 A1 | 9/2007 |
| WO | WO 2011/039227 A2 | 4/2011 |
| WO | WO 2012/017035 A1 | 2/2012 |
| WO | WO 2012/049484 A2 | 4/2012 |
| WO | WO 2012/103140 A1 | 8/2012 |
| WO | WO 2013/063707 A1 | 5/2013 |

\* cited by examiner

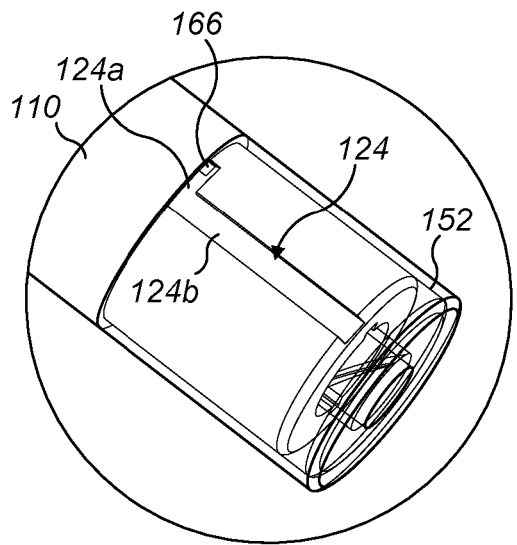
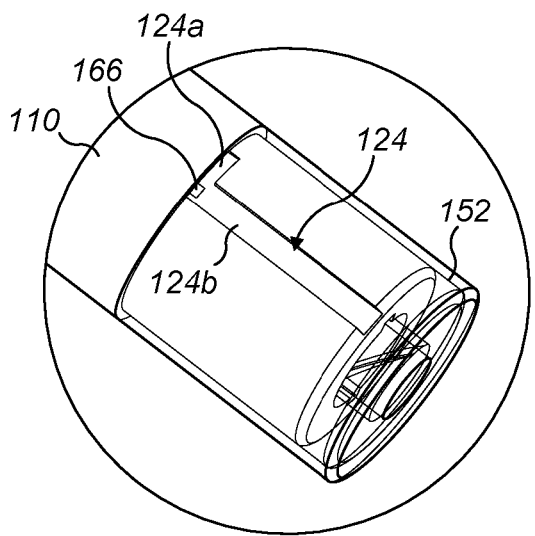
FIG. 6(a)    FIG. 6(b)
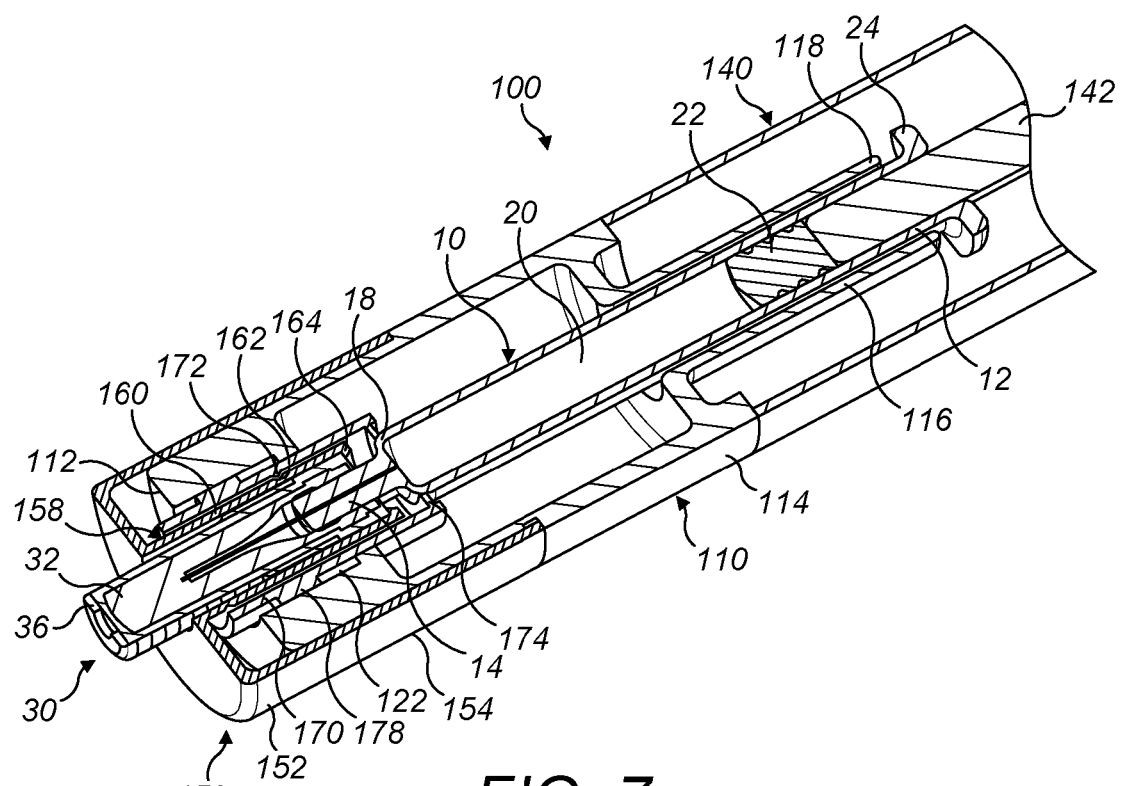
FIG. 7

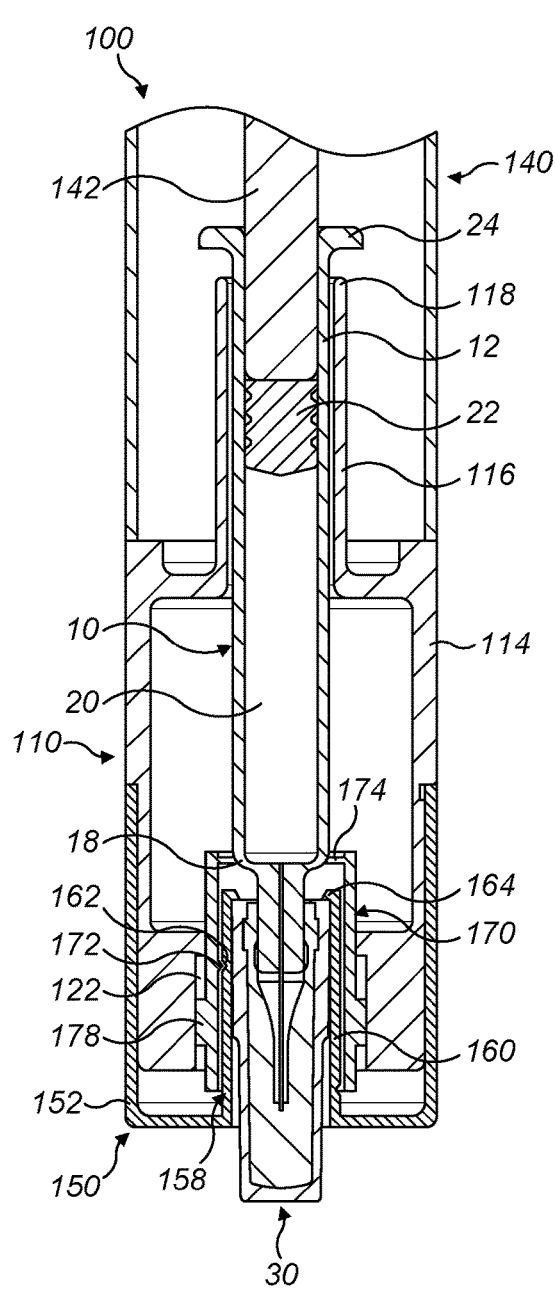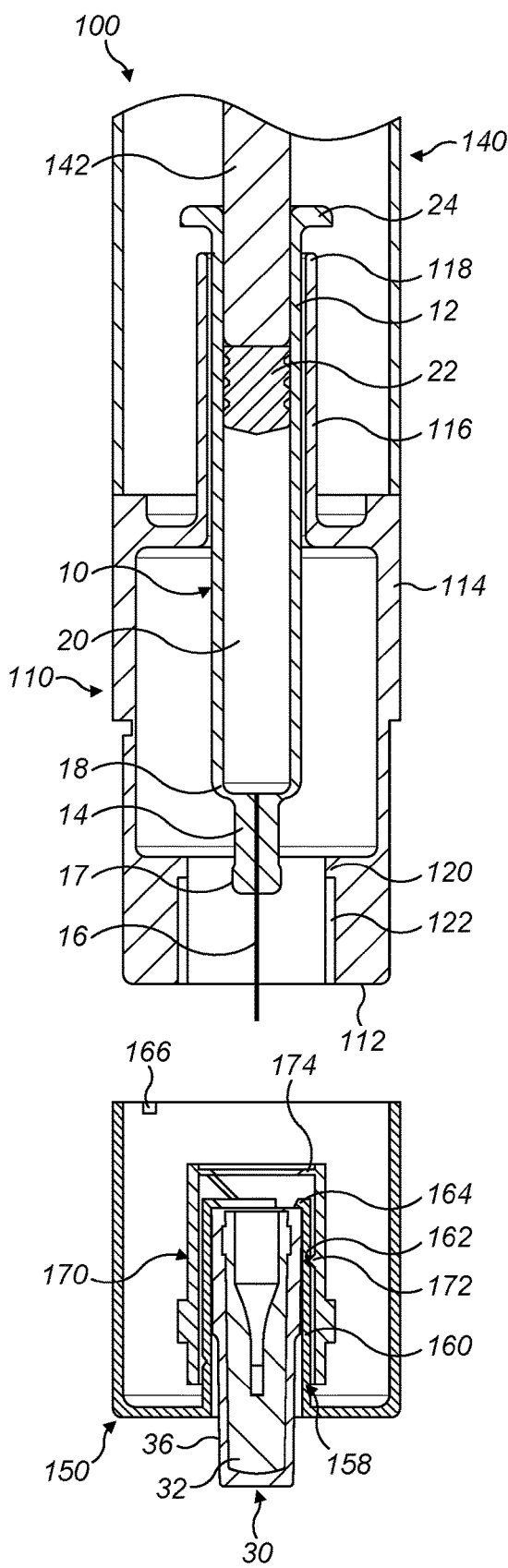
FIG. 8
FIG. 9

PRIMING ARRANGEMENT FOR DRUG DELIVERY DEVICE

The present application is a § 371 submission of international application PCT/GB2016/052573, filed 19 Aug. 2016 and entitled Injection Device, which claims the benefit of the filing date of GB 15 14827.3, filed 20 Aug. 2015.

The present invention relates to an injection device suitable for the delivery of a medicament to a patient. In particular, but not exclusively, the invention relates to a single-use injection device for hypodermic injection of a predetermined dose of medicament from a pre-filled container.

Injection devices designed for automatic or semi-automatic delivery of a single pre-determined dose of a medicament are known in the art. Such devices typically include a housing that allows the user to grip the device, a pre-filled syringe containing the medicament, and a firing mechanism. The pre-filled syringe includes a tubular glass barrel with a staked hypodermic needle at its distal end, a needle shield to shroud the needle, and a stopper slidably received in the barrel. The needle shield is typically of two-part construction, with an elastomeric inner part for receiving the needle and a rigid outer cap or cover, for example of polypropylene, which is attached to the inner part and can be gripped by a user to pull the shield off the needle. This shield arrangement is known in the art as a rigid needle shield (RNS). One or more radially-projecting flanges are provided on the proximal end of the syringe barrel, which can be used to retain the syringe in the device. One example of a pre-filled syringe with a rigid needle shield is available under the registered trade mark Hypak (Becton Dickinson, N.J., USA).

With the syringe in place in the housing of the device, the distal end of the housing is closed by a cap. To prepare the device for use, the cap is removed. The cap is arranged to grip the rigid needle shield, so that removal of the cap pulls the rigid needle shield off the needle. The distal end of the housing is then placed against the skin. When activated, a plunger of the firing mechanism pushes the stopper of the syringe distally towards the needle to inject the medicament. In some devices, known as auto-injectors, needle insertion is also automatic. In such devices, the needle is initially retracted in the housing and the firing mechanism also causes the syringe to move to advance the needle out of the housing and into the patient's skin before injection of the medicament.

Examples of such devices are described in the Applicant's International Patent Application Publication No. WO 2012/049484 and UK Patent Application Publication No. GB 2516624, the contents of which are incorporated herein by reference.

The use of pre-filled syringes in auto-injectors and in other injection devices has several advantages. Such syringes are relatively inexpensive and have been validated for compatibility and safety for many existing medicaments. Furthermore, once the medicament has been sealed in the syringe between the stopper at one end and the needle shield at the other end, the sterility of the needle and the medicament can be maintained throughout assembly and subsequent handling of the device until the needle shield is removed to prepare the device for use.

One potential limitation of the use of pre-filled syringes in injection devices is that the amount of medicament delivered can vary between nominally identical devices. In most cases, when the device is activated, the plunger moves the stopper from its initial position along the whole length of the syringe barrel, to expel substantially the whole volume of the medicament from the syringe. The amount of medicament delivered is therefore dependent on the initial position of the stopper of the syringe relative to the syringe barrel.

In practice, due to manufacturing tolerances and variations in the filling process for pre-filled syringes, the initial position of the stopper with respect to the syringe body, and therefore the amount of medicament contained in the syringe, may vary between syringes by a relatively large degree. For example, a variation in the initial stopper position of +/−1 mm from a nominal target position may be expected. Accordingly, for a permissible tolerance in the stopper position of +/−1 mm, the actual stroke of the stopper could vary in length by up to 2 mm. This can give rise to undesirable variability in the dose delivered, which is particularly significant when the total quantity of medicament to be delivered is small.

It would therefore be desirable to provide an injection device that can deliver a more accurate quantity of medicament from a pre-filled container, such as a syringe, irrespective of variations in the initial position of the stopper of the pre-filled container.

Against this background, and from a first aspect of the present invention, there is provided an injection device for injection of a medicament from a pre-filled container having a container body for containing the medicament, a needle disposed at a distal end of the container body, a removable needle shield and a stopper for expelling medicament from the container. The device comprises a housing for housing the container, a plunger for driving the stopper of the container in a distal direction to expel the medicament, and a priming mechanism having an operating member that is movable with respect to the housing. The priming mechanism is arranged to release the needle shield from the needle and to move the container body in a proximal direction with respect to the plunger upon movement of the operating member from a first position to a second position during an operating sequence of the device.

By moving the container body in the proximal direction, the stopper of the container can be brought into contact with the plunger or a priming member of the device to move the stopper distally with respect to the container body. In this way, the stopper can be moved into a pre-determined, primed position that is at a known distance from the ends of the container body, to eliminate any variation in the volume of medicament expelled from the container during the subsequent injection. The injection device of the present invention therefore delivers an accurate dosage of medicament that is not dependent on the initial position of the stopper of the container after manufacture. The container may be a pre-filled syringe.

The priming mechanism releases the needle shield to unseal the needle and allow medicament to be displaced through the needle during movement of the stopper to the primed position. The displaced medicament may be captured in the needle shield. Because the priming mechanism is operated by the user during the operating sequence of the device, the needle shield can remain in place to maintain the sterility of the needle and the medicament for as long as possible. Furthermore, the stopper can be moved into the primed position just before use of the device, eliminating potential further movement of the stopper during transportation or handling of the device.

The priming mechanism may be arranged to prevent movement of the needle shield in the proximal direction when the container body is moved in the proximal direction with respect to the plunger. With this arrangement, the needle shield can be released from the needle upon movement of the container body in the proximal direction.

To this end, the device may comprise at least one holding member for preventing or blocking movement of the needle shield in the proximal direction when the operating member is moved from the first position to the second position. In this way, when the container body moves in the proximal direction, the needle of the container is pulled away from the needle shield to allow medicament to be expelled from the needle as the stopper moves to its primed position.

The or each holding member can be attached to any suitable part of the device. For example, the or each holding member may be attached to the operating member or to the housing.

In another configuration, the priming mechanism may be arranged to move the needle shield in the distal direction with respect to the housing to release the needle shield from the needle. Preferably, the priming mechanism is arranged to move the needle shield in the distal direction with respect to the housing before moving the container body in the proximal direction with respect to the plunger. In this way, the needle shield can be released before the stopper is displaced to its primed position, ensuring that the displaced medicament can be discharged from the needle.

The priming mechanism may be arranged to move the needle shield in the distal direction with respect to the housing upon movement of the operating member from the first position to an intermediate position, and to move the container body in the proximal direction with respect to the plunger upon movement of the operating member from the intermediate position to the second position.

Preferably, the operating member comprises a removable cap for closing a distal end of the housing. In this way, operation of the priming mechanism can be driven by movement of the cap, which minimises the number of device components that the user must interact with to prepare the device for use.

It is particularly preferred if the action required by the user to move the cap from the first position to the second position to operate the priming mechanism is incorporated into the action required to remove the cap from the device, so as to minimise the number of user actions needed to prepare the device for use.

For example, movement of the cap from the first position to the second position may comprise an unlocking movement of the cap. Accordingly, in one embodiment, when the cap is in its first position, the cap is locked against removal from the housing and, when the cap is in its second position, the cap is unlocked for removal from the housing.

The cap may, for example, be engaged with the housing with a bayonet-type fitting, in which a turning force is first applied to the cap to unlock the cap and to cause priming of the container, and then a pulling force is applied to the cap in the distal direction to remove the cap from the housing. Alternatively, the cap may be engaged with the housing in a different way. For example, the cap may be moved first in a proximal direction with respect to the housing to prime the container and then in a distal direction to remove the cap from the housing. In another example, the cap is turned and simultaneously moved in proximal and/or distal directions to remove the cap from the housing. The cap may comprise a shield retainer to retain the shield in the cap when the cap is removed from the device so that the needle shield is automatically removed when the cap is removed. Conveniently, when a holding member for preventing or blocking movement of the needle shield in the proximal direction is provided, the shield retainer may comprise the holding member. Said another way, the shield retainer of the cap may be arranged both to prevent movement of the needle shield in the proximal direction when the priming mechanism operates, and to grip the shield for removal with the cap.

The device may comprise a carrier part arranged to cooperate with the container body to move the container body in the proximal direction with respect to the plunger. For example, the carrier part may be arranged to cooperate with a shoulder of the container body. The carrier part may comprise a collar, one or more projections, one or more ribs, or any other suitable formation or combination of formations.

When the priming mechanism is arranged to release the needle shield by moving the needle shield in the distal direction, the carrier part may also be arranged to cooperate with the needle shield to release the needle shield from the needle. For example, the priming mechanism may cause the carrier part first to move distally with respect to the housing to move the needle shield in the distal direction, and then to move proximally with respect to the housing to move the container body in the proximal direction.

The carrier part may be associated with or attached to the operating member. For example, when the operating member comprises a cap having a shield retainer, the shield retainer may comprise the carrier part.

Movement of the operating member from the first position to the second position may comprise a turning movement. In this way, the user of the device can apply a turning movement to the operating member whilst holding the housing (or a part connected to the housing) to operate the priming mechanism. The turning movement of the operating member may be a simple turning movement with no axial component, or the turning movement may be accompanied by axial movement of the operating member in the proximal and/or the distal direction over part or all of the movement from the first position to the second position.

To convert the turning movement of the operating member to proximal movement of the container body, the priming mechanism may comprise a shuttle member arranged to cooperate with the operating member and the container body. The shuttle member may be generally tubular for cooperation with a cylindrical or part-cylindrical surface of the operating member.

The device may comprise an inclined formation for moving the shuttle member in the proximal direction upon movement of the operating member from the first position to the second position. Proximal movement of the shuttle member may occur during the whole of the movement of the operating member from the first position to the second position, or during only a part of the movement of the operating member from the first position to the second position. The inclined formation may be disposed on the operating member or on the shuttle member. For example, the inclined formation may comprise a helical groove or projection on the operating member for cooperation with a corresponding projection or groove of the shuttle member. The helical groove and projection may extend around the shuttle member in a thread formation. In another embodiment, the inclined formation comprises a ramp for cooperation with a surface of the shuttle member.

The shuttle member may be further arranged to cooperate with the needle shield to release the needle shield from the needle. The operating member may be coupled to the shuttle member such that movement of the operating member from the first position to an intermediate position causes movement of the shuttle member in the distal direction to cooperate with the needle shield.

Thus, in another example, the device comprises a first inclined formation arranged to move the shuttle member in the distal direction upon turning movement of the operating member from the first position to an intermediate position to release the needle shield and a second inclined formation arranged to move the shuttle member in the proximal direction upon turning movement of the operating member from the intermediate position to the second position to move the container body in the proximal direction.

When a carrier part is provided, the shuttle member may comprise the carrier part. The carrier part may, for example, comprise a collar, or one or more tabs, ribs or other suitable formations. The carrier part may be disposed at the periphery of an aperture in the shuttle member for receiving a distal part of the container body.

Guide means may be provided for preventing rotation of the shuttle member with respect to the housing when the operating member is moved from the first position to the second position. For example, the shuttle member may include guide pins that cooperate with longitudinally-extending channels provided in the housing. In another configuration, the shuttle member includes the channels and the housing includes the guide pins.

In another arrangement, the operating member may be arranged to cooperate with the container body to move the container body in the proximal direction.

In this case, a shuttle member need not be provided. The carrier part, when present, may be provided on the operating member (as in the example described above, in which the operating member comprises a cap and the carrier part is disposed on a shield retainer of the cap).

The device may comprise an inclined formation arranged to move the operating member in the proximal direction upon turning movement of the operating member. In one example, the device comprises a first inclined formation arranged to move the operating member in the distal direction upon turning movement of the operating member from the first position to an intermediate position to release the needle shield and a second inclined formation arranged to move the operating member in the proximal direction upon turning movement of the operating member from the intermediate position to the second position to move the container body in the proximal direction.

In more general terms, when a carrier part for cooperation with the container body and the needle shield is provided, the device may include a first guide formation arranged to move the carrier part in the distal direction upon turning movement of the operating member from the first position to an intermediate position to release the needle shield, and a second guide formation to move the carrier part in the proximal direction upon turning movement of the operating member from the intermediate position to the second position to move the container body in the proximal direction. The first and/or second guide formations may be inclined with respect to the axis of the device to convert turning movement of the operating member into distal and/or proximal movement of the carrier part. The first and/or second guide formations may be arranged to guide movement of the operating member with respect to the housing. When a shuttle member is present, the first and/or second guide formations may be arranged to drive movement of the shuttle member with respect to the operating member and/or the housing in response to movement of the operating member.

When the operating member comprises one or more holding members to prevent movement of the needle shield in the proximal direction, the or each holding member may be slidably attached to the operating member to permit turning movement of the operating member with respect to the needle shield.

In this way, when the operating member is turnable to operate the priming mechanism, the needle shield is not forced to rotate with respect to the container body. This reduces the risk of the needle becoming blocked or otherwise damaged due to rotation of the needle in the needle shield.

For the same reason, the device may comprise slip means, such as a low-friction washer, a low-friction coating, and/or a small contact area protrusion, for reducing friction between the or each holding member and the needle shield. Alternatively, or in addition, the device may include a resistance member arranged to prevent turning movement of the shield with respect to the container body. When a shuttle member is provided, for example, the resistance member may comprise a projection on the shuttle member that presses against the needle shield.

In another embodiment, movement of the operating member from the first position to the second position comprises an axial or longitudinal movement. For example, the operating member may be movable in the proximal direction with respect to the housing in order to operate the priming mechanism. In another example, the operating member may be movable first in the distal direction and then in the proximal direction to operate the priming mechanism.

Stop means may be provided to define the second position of the operating member. For example, a surface of the operating member may come into contact with a surface of the housing when the operating member reaches the second position.

When a shuttle member is provided, the cap may engage with the shuttle member so that the shuttle member is retained by the cap when the cap is removed. Alternatively, the shuttle member may disengage from the cap and may be retained in the housing when the cap is removed.

The device may comprise guide means for guiding movement of the operating member between the first position and the second position. For example, the operating member may include a key for engagement in a corresponding keyway of the housing, or the operating member may include a keyway for engagement with a key provided on the housing. When one or more inclined formations are provided to control movement of the operating member, the guide means may comprise the or each inclined formation.

The injection device may comprise a drive mechanism arranged to hold the plunger in a starting position and to drive the plunger in a distal direction with respect to the housing to expel medicament from the container upon activation of the drive mechanism.

The priming mechanism may be arranged to push the stopper of the container against a priming member upon movement of the operating member from the first position to the second position.

The priming member may comprise the plunger. Alternatively, the priming member and the plunger may be separate components, in which case the plunger may be movable with respect to the priming member. This arrangement can be beneficial when it is desirable to adapt the device for use with containers with different initial fill volumes, for example to provide different doses of medicament. In particular, when a separate priming member is provided, the length of the priming member can be selected to suit any particular initial fill volume, whilst the length and stroke of the plunger can remain the same for all fill volumes. Furthermore, greater precision in the dimensions and position of a separate priming member may be achievable, resulting in greater accuracy when moving the stopper into its primed position compared to when the plunger is used as the priming member.

In one embodiment, the plunger comprises a bore and the priming member comprises a rod received in the bore.

When the plunger is held in its starting position, for example by a drive mechanism, a distal end of the priming member is preferably disposed distally with respect to the plunger for contact with the stopper of the container when the plunger is in its starting position.

The priming member may be attached to the housing. Furthermore, the priming member may be detachable from the housing upon movement of the plunger in the distal direction. The plunger may be arranged to carry the priming member in the distal direction upon movement of the plunger in the distal direction. For example, the priming member may comprise a contact formation, such as a contact disc, to engage with a distal end face of the plunger. The contact formation may be disposed at the distal end of the plunger, and may be receivable in a recess in the distal end face of the plunger, so that the plunger can directly contact the stopper of the container during delivery of the medicament. In another arrangement, the priming member contacts the stopper of the container during delivery of the medicament.

The device may comprise a container guide for receiving the container body. The container guide may be movable with respect to the housing between a retracted position and an advanced position in which the container is positioned for injection of the medicament. For example, when the container includes a needle, in the advanced position the needle may project from a distal end of the housing. The injection device may be an auto-injector with a drive mechanism arranged first to move the container guide from the retracted position to the advanced position, and then to move the stopper of the container for injection of the medicament.

The plunger of the device may be adjustable in length, so that the device can be adapted for use with different containers that are pre-filled with varying amounts of medicament. For example, the plunger may comprise cooperating proximal and distal parts, such as a proximal tubular holder part for receiving a distal rod part, and engagement means for locking the proximal and distal parts together to a desired length.

The present invention also extends to injection device according to the first aspect of the invention and fitted with a pre-filled container comprising a syringe having a syringe body for containing the medicament, a needle disposed at a distal end of the syringe body, a removable needle shield and a stopper for expelling medicament through the needle.

In another aspect, the invention resides in an injection device for injection of a medicament from a pre-filled container having a container body for containing the medicament, and a stopper for expelling medicament from the container. The device comprises a housing for housing the container, a plunger for driving the stopper of the container in a distal direction to expel the medicament, and a priming mechanism having an operating member that is movable with respect to the housing. The priming mechanism is arranged to move the container body in a proximal direction with respect to the plunger upon movement of the operating member from a first position to a second position.

Preferably, movement of the operating member from the first position to the second position comprises or incorporates a turning movement, and movement of the operating member is performed during an operating sequence of the device.

The injection device may comprise a drive mechanism arranged to hold the plunger in a starting position and to drive the plunger in a distal direction with respect to the housing to expel medicament from the container upon activation of the drive mechanism.

The priming mechanism may be arranged to push the stopper of the container against a priming member upon movement of the operating member from the first position to the second position.

The priming member may be cooperable with a plunger of the device. For example, the priming member may comprise a rod, and the priming member may be received in a bore of the plunger. The plunger may be movable with respect to the priming member. When the plunger is held in its starting position, for example by a drive mechanism, a distal end of the priming member is preferably disposed distally with respect to the plunger for contact with the stopper of the container when the plunger is in its starting position. The priming member may be attached to the housing, and may be detachable from the housing upon movement of the plunger in the distal direction. The plunger may be arranged to carry the priming member in the distal direction upon movement of the plunger in the distal direction.

The container may comprise an outlet for medicament and a closure for sealing the outlet. The priming mechanism may be arranged to cooperate with the closure and/or the container body to open the outlet, for example by breaking the seal between the closure and the outlet. The outlet may comprise a needle, and the closure may comprise a needle shield.

Aspects and embodiments of the present invention may be used for the delivery of medicaments comprising or including pharmaceutical products (active ingredients).

Pharmaceutical products (active ingredients) contemplated for use include small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. In addition, active ingredients of the present invention can be perceptible. A wide range of active ingredients are contemplated. These include but are not limited to hormones, cytokines, hematopoietic factors, growth factors, antiobesity factors, trophic factors, anti-inflammatory factors, and enzymes. One skilled in the art will readily be able to adapt a desired active ingredient to the necessary formulations encompassed by the present invention.

Active ingredients can include but are not limited to insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies. The term proteins, as used herein, includes peptides, polypeptides, consensus molecules, analogs, derivatives or combinations thereof.

Active ingredients include any extended half-life variants of the active ingredient listed herein or analogues thereof. Thus, the active ingredients can be any long acting variants of the active ingredient listed herein or analogues thereof. In some embodiments, the active ingredient include any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

Preferred and/or optional features of each aspect and embodiment of the invention may be used, alone or in appropriate combination, in the other aspects and embodiments also.

Embodiments of the present invention will now be described, by way of example only, with reference to the accompanying drawings in which like reference numerals are used for like features, and in which:

FIG. 1 is an exploded isometric view of part of an injection device according to a first embodiment of the present invention;

FIGS. 2(a) and 2(b) are cross-sectional views of the injection device of FIG. 1 on two perpendicular planes;

Figure 1:
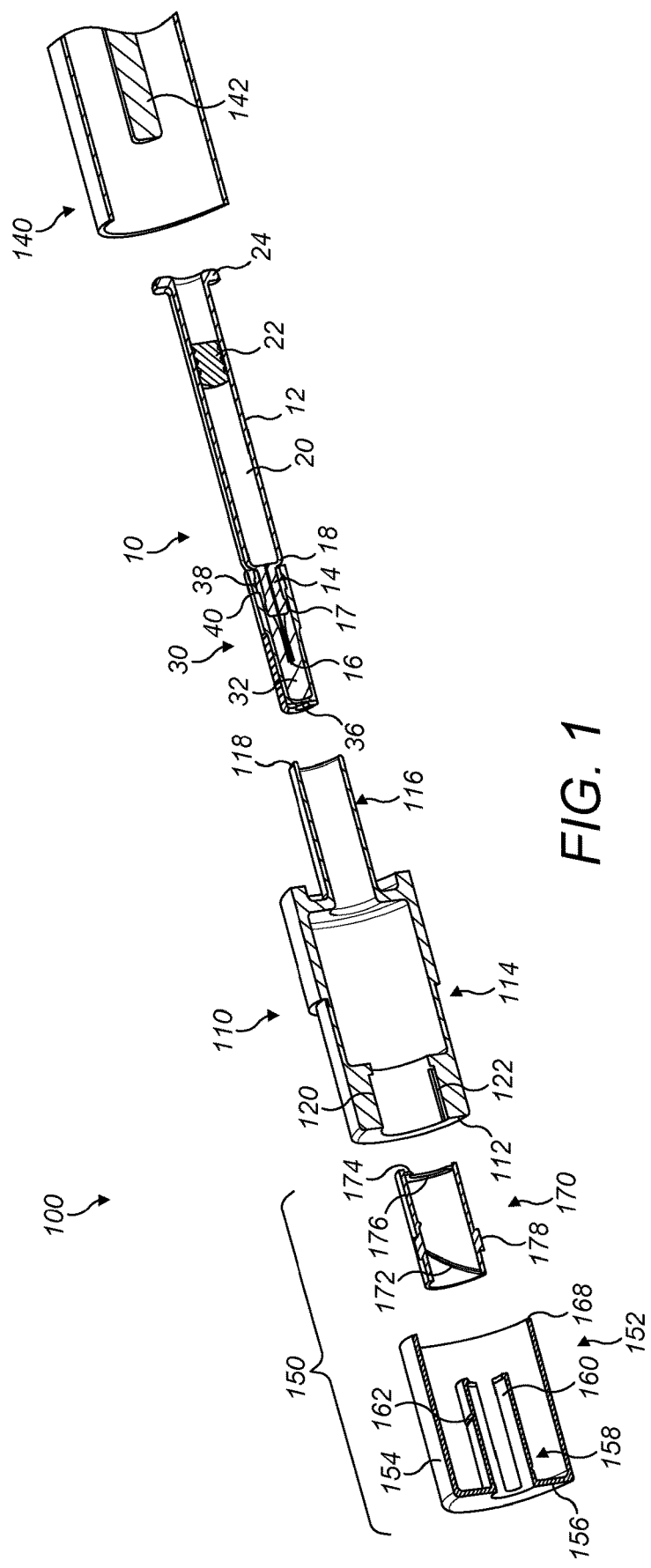
Figure 10C:
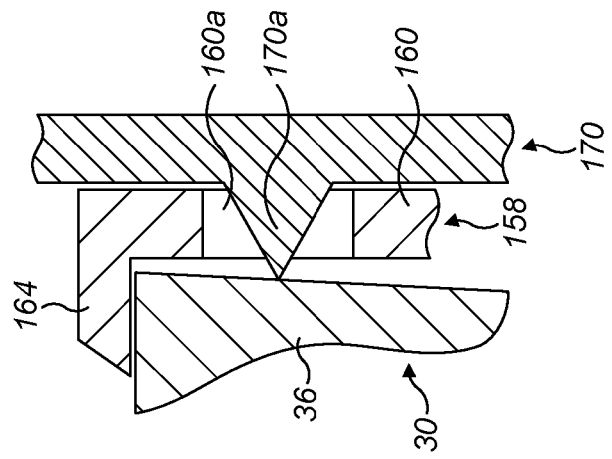
Figure 10B:
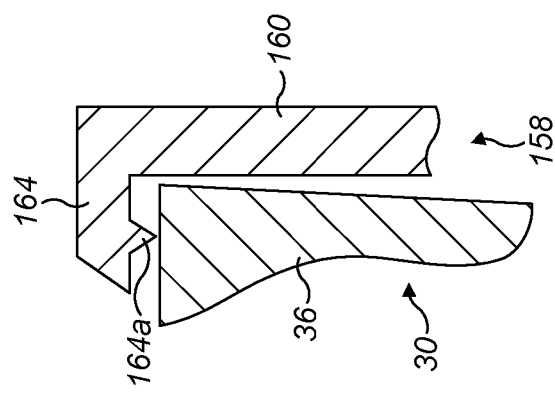
Figure 10A:
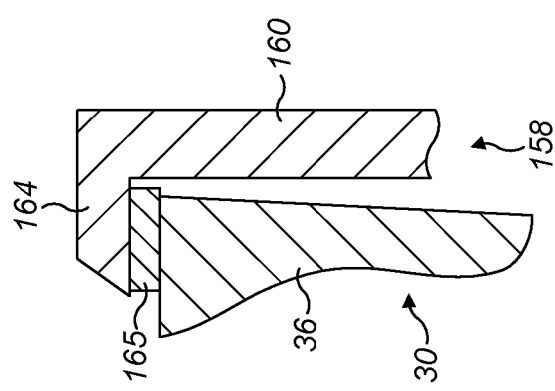
Figure 11:
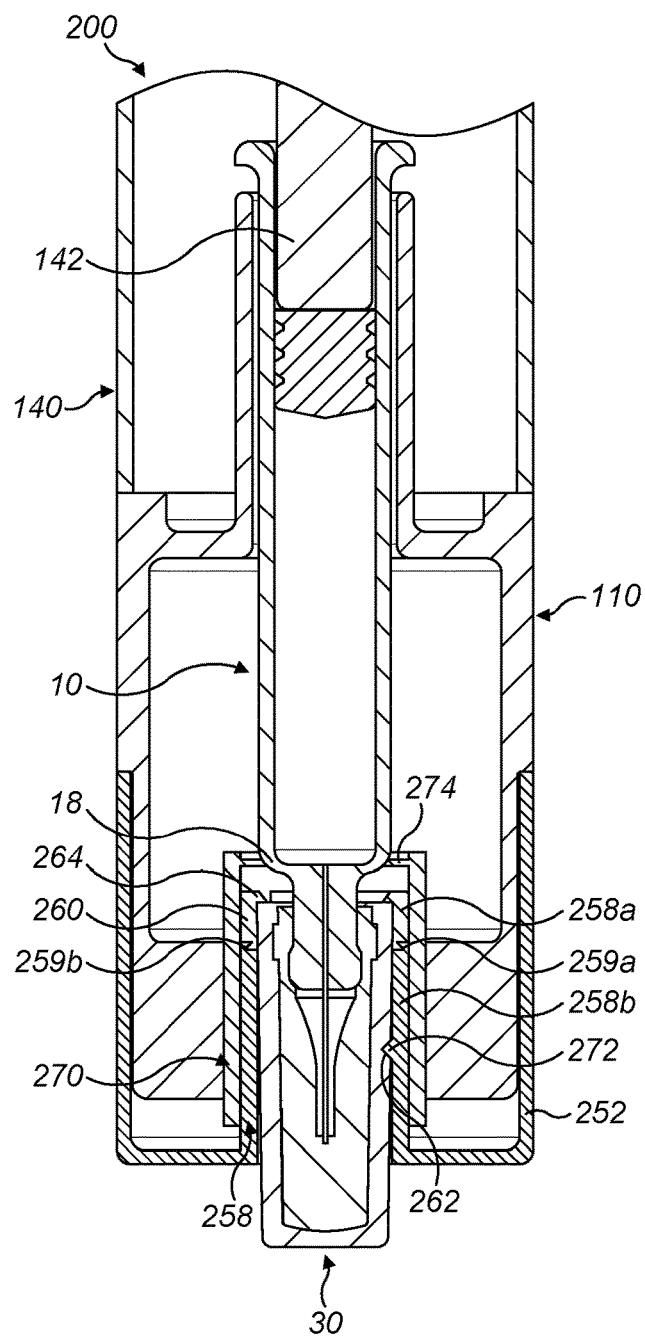
Figure 12:
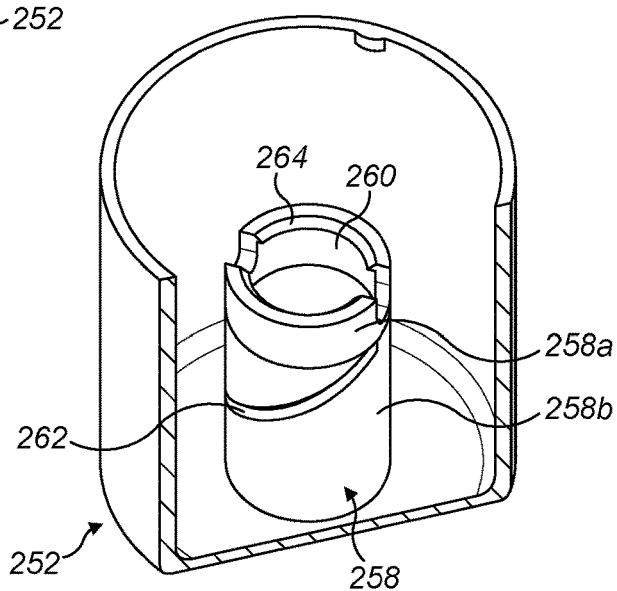
Figure 13A:
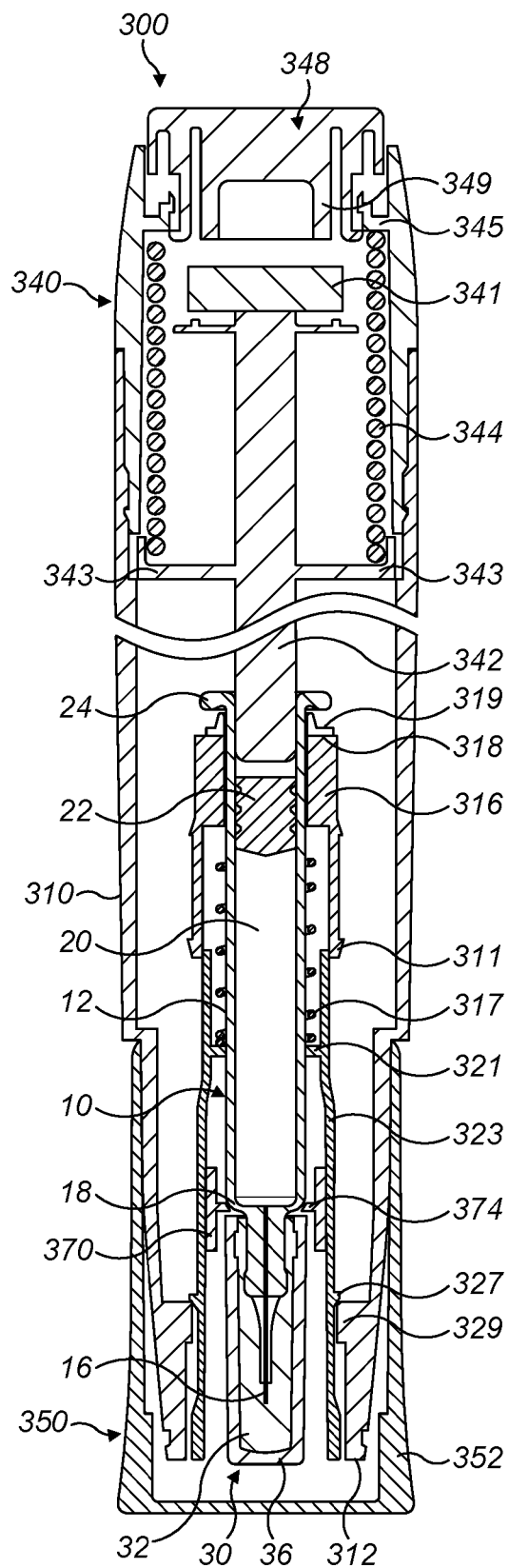
Figure 13B:
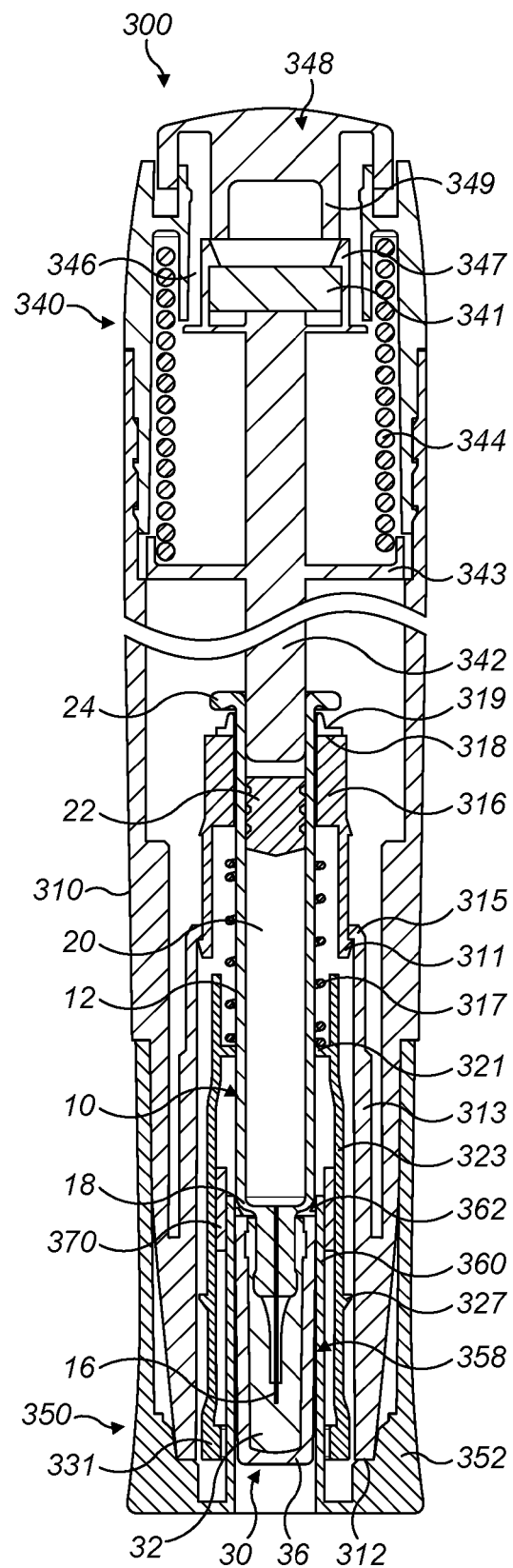
Figure 14:
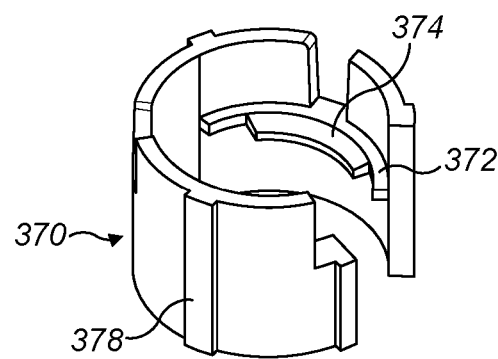
Figure 15:
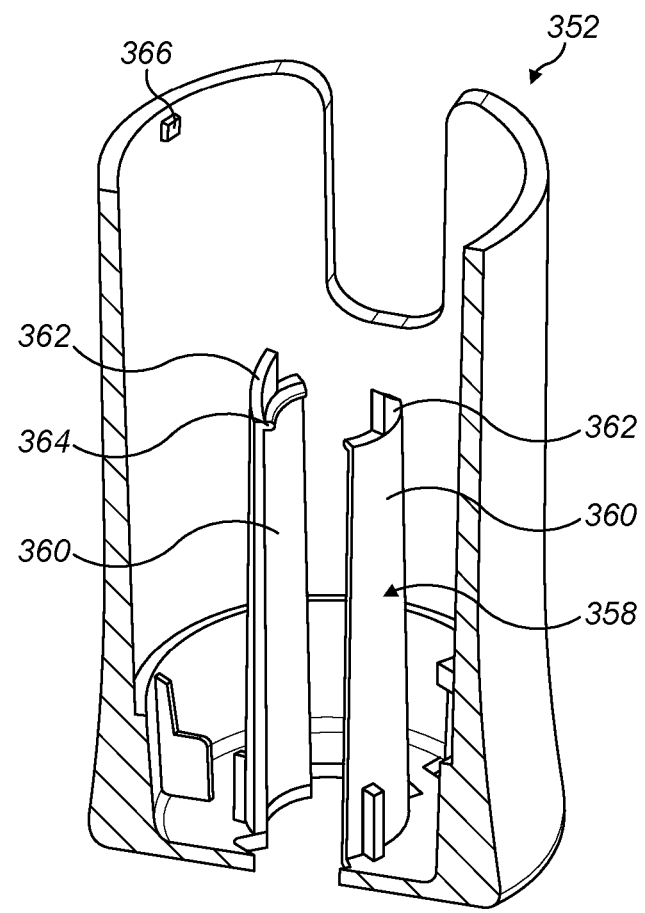
Figure 16A:
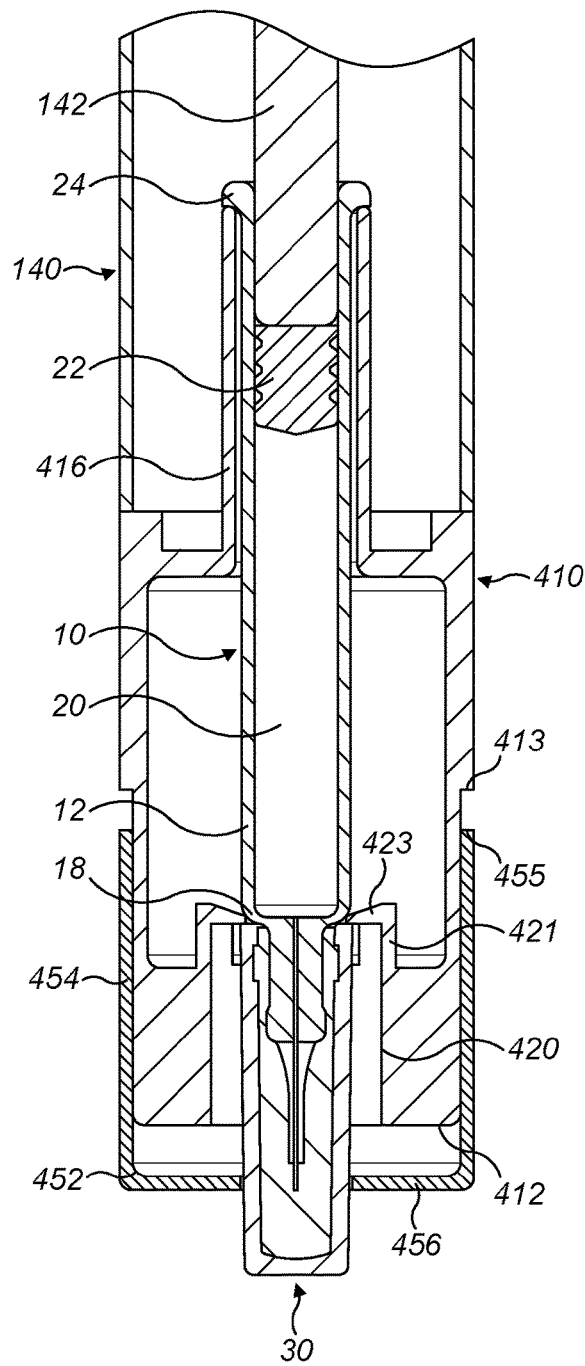
Figure 16B:
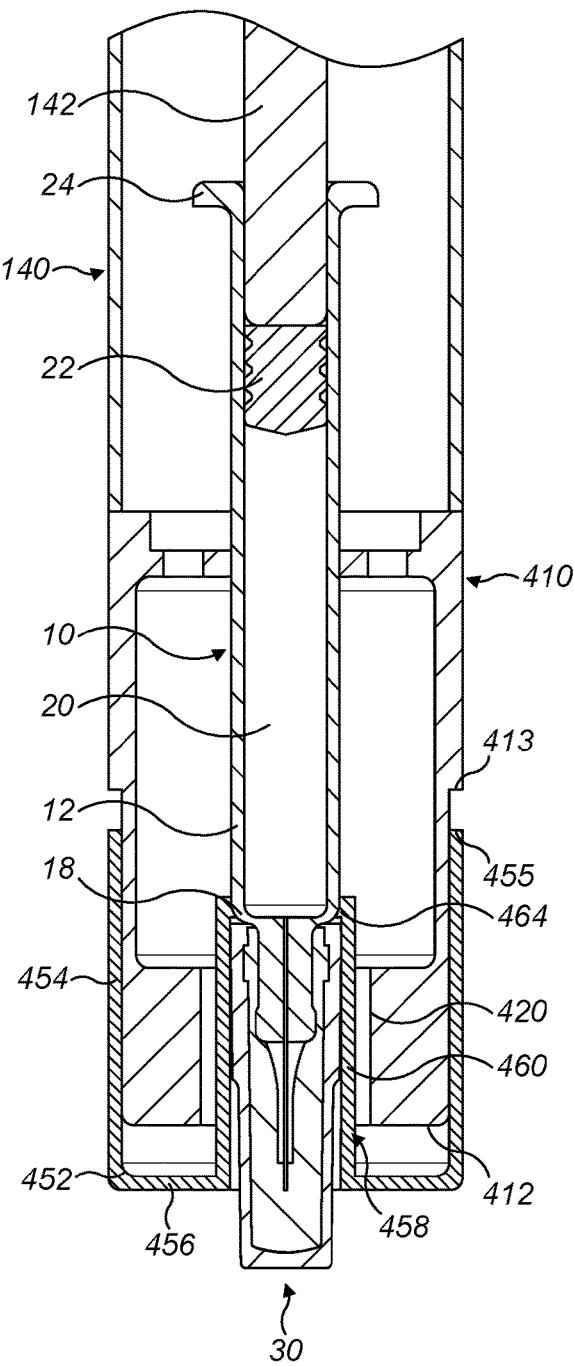
Figure 17A:
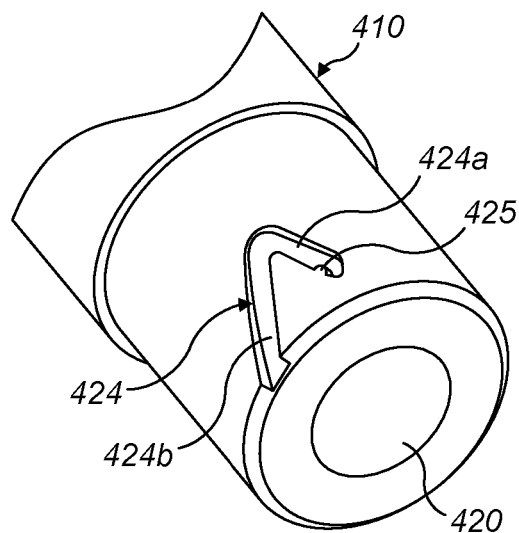
Figure 17B:
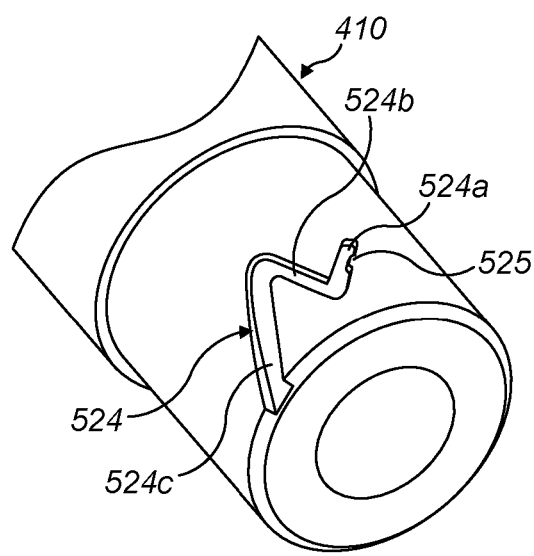
Figure 18A:
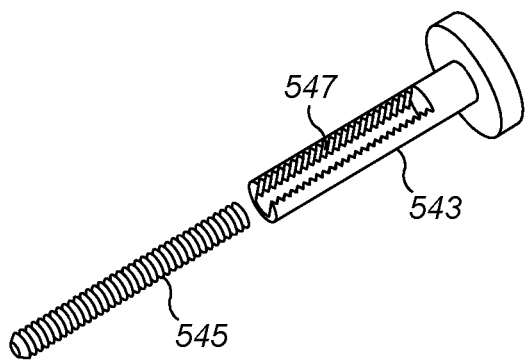
Figure 18B:
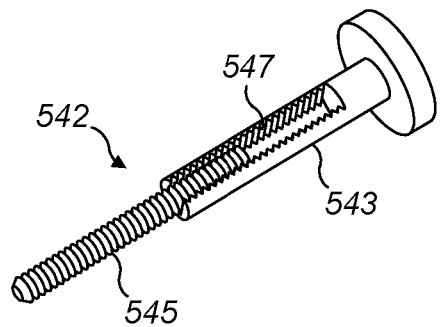
Figure 19A:
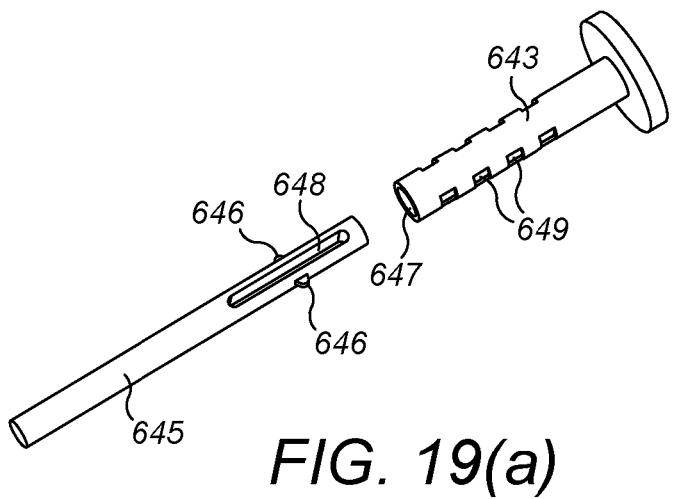
Figure 19B:
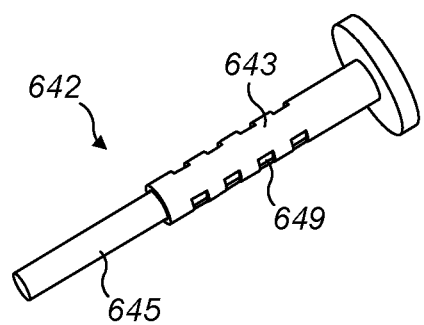
Figure 20:
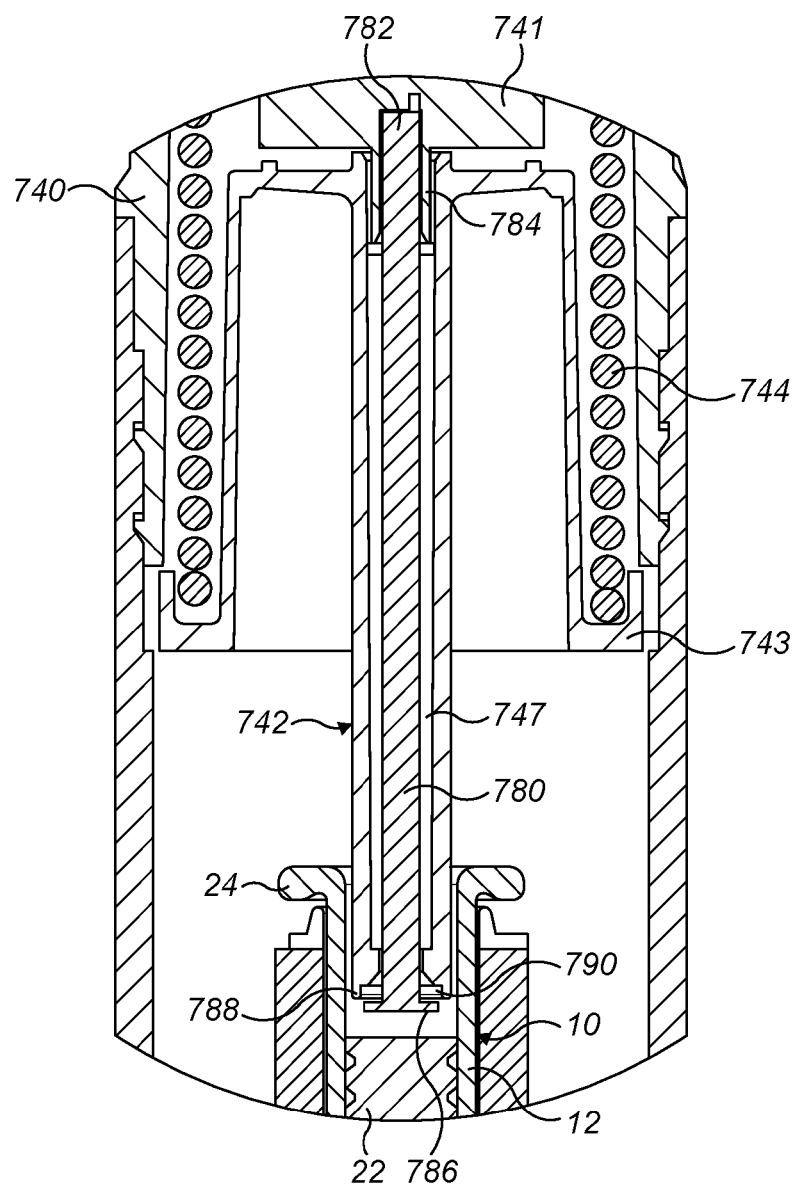

FIGS. 6(a) and 6(b) are isometric views of part of the injection device of FIG. 1, with the cap component in a first position and in a second position, respectively;

FIG. 7 is a cut-away view of the injection device of FIG. 1, with the cap component in the second position;

FIG. 8 is a cross-sectional view of the injection device of FIG. 1, with the cap component in the second position;

FIG. 9 is a cross-sectional view of the injection device of FIG. 1, with the cap component removed;

FIGS. 10(a), 10(b) and 10(c) are schematic cross-sectional views showing variants of the injection device of FIG. 1;

FIG. 11 is a cross-sectional view of part of an injection device according to a second embodiment of the present invention;

FIG. 12 is a cut-away isometric view of a cap component of the injection device of FIG. 11;

FIGS. 13(a) and 13(b) are cross-sectional views of an injection device according to a third embodiment of the present invention on two perpendicular planes;

FIG. 14 is an isometric view of a shuttle member of the injection device of FIGS. 13(a) and 13(b);

FIG. 15 is a cut-away isometric view of a cap component of the injection device of FIGS. 13(a) and 13(b);

FIGS. 16(a) and 16(b) are cross-sectional views of part of an injection device according to a fourth embodiment of the present invention on two perpendicular planes;

FIGS. 17(a) and 17(b) are isometric views showing housing components of first and second variants of the device of FIG. 16;

FIGS. 18(a) and 18(b) are exploded and assembled isometric views of a first plunger component for use in an injection device according to the present invention;

FIGS. 19(a) and 19(b) are exploded and assembled isometric views of a second plunger component for use in an injection device according to the present invention; and FIG. 20 is a cross-sectional view of part of an injection device according to a fifth embodiment of the present invention.

FIGS. 1 to 9 show an injection device 100 according to a first embodiment of the invention. The injection device is arranged to deliver a single dose of medicament from a pre-filled container, which in this example is a syringe 10. Throughout the following description, the terms "front", "distal" and related terms are used to refer to the end of the device that is towards the patient's skin in use (i.e. the lower end of the device in FIGS. 2(a) and 2(b)), and the terms "rear", "proximal" and related terms are used to refer to the end of the device that is furthest from the skin in use (i.e. the upper end of the device in FIGS. 2(a) and 2(b)). Terms such as "turning" and "rotation" are intended to describe turning movement around the longitudinal axis of the device (i.e. the vertical axis in FIGS. 2(a) and 2(b)), except if the context demands otherwise.

Referring first to FIG. 1, the device 100 includes a generally elongate two-part housing comprising a front housing body 110 for carrying the syringe 10, and a rear housing body 140 that houses a piston or plunger 142 and a drive mechanism (not shown) for the plunger 142. The device also includes a cap assembly 150 including an outer cap 152 and a shuttle member 170. The cap assembly 150 closes a distal end 112 of the front housing body.

The syringe 10 is preferably of a type known in the art, for example a Hypak syringe. The syringe 10 comprises a generally tubular glass body or barrel 12. At its distal end, the barrel 12 is formed into a reduced-diameter end portion 14 that carries a staked hypodermic needle 16. The end portion 14 includes a collar 17, and a shoulder 18 of the barrel 12 is formed where the end portion 14 meets the remaining portion of the barrel 12. The barrel 12 is filled with a quantity of medicament 20 and is closed by a stopper 22 that is slidably received in the barrel 12. An outwardly-projecting flange 24 is provided at the proximal end of the barrel 12.

Figure 2A:
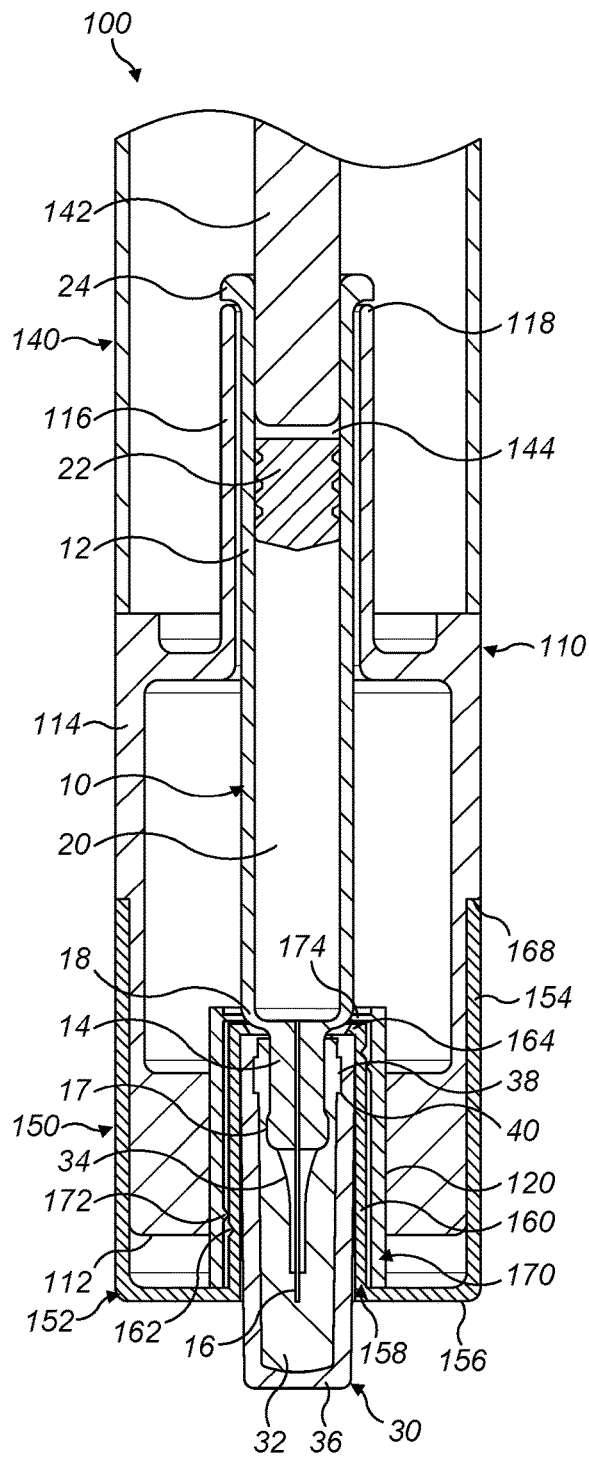
Figure 2B:
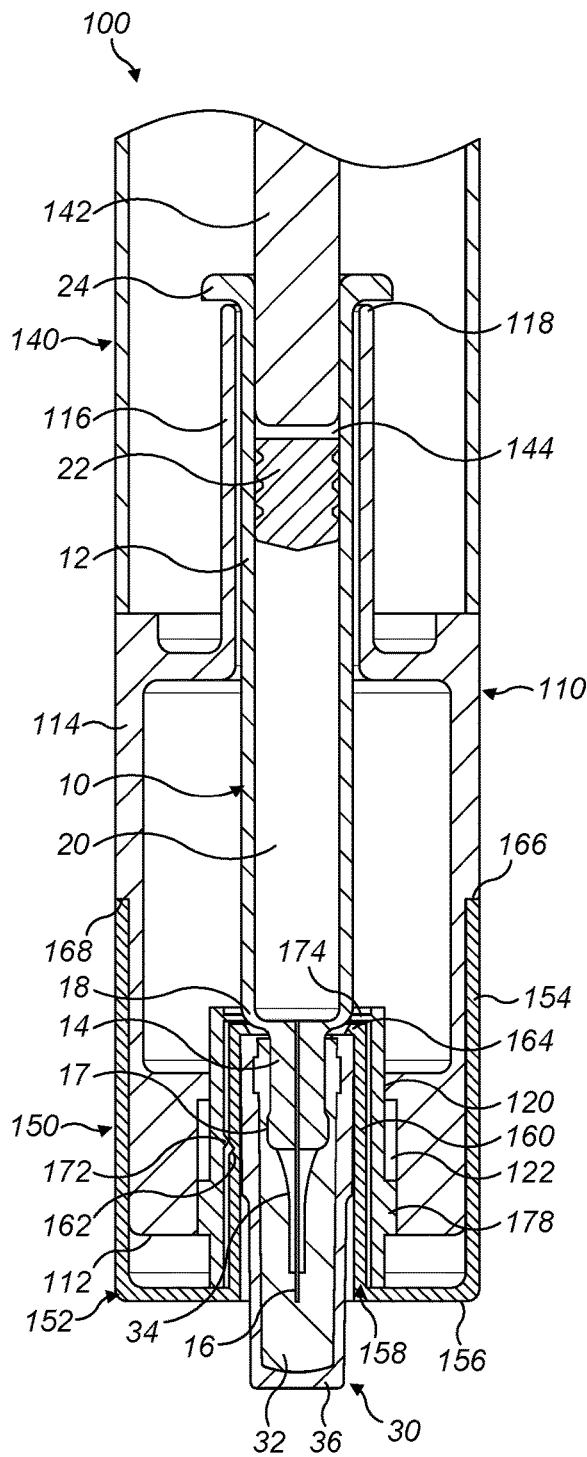

As known in the art, a rigid needle shield 30 is removably attached to the distal end portion 14 of the syringe 10. Referring additionally to FIGS. 2(a) and 2(b), which show the device 100 in cross-section in two perpendicular planes, the rigid needle shield 30 comprises an elastomeric insert or inner shield 32 having a funnel-shaped cavity 34 into which the needle 16 can be inserted, and a rigid outer cap or cover 36. The inner shield 32 has a collar 38 on its outside surface that engages with recesses 40 in the cover 36, to attach the inner shield 32 to the cover 36. The cover 36 is made from a rigid plastics material, such as polypropylene, and the inner shield 32 is made from a natural or synthetic rubber.

When the rigid needle shield 30 is fitted to the syringe 10, the reduced-diameter end portion 14 of the syringe barrel 12, with the collar 17, is received in the proximal end of the cavity 34 of the inner shield 32. The cavity 34 is under-sized with respect to the end portion 14, so that the inner shield 32 conforms to and grips the end portion 14 of the barrel 12 around the collar 17. In this way, the rigid needle shield 30 is retained on the syringe 10 and an air-tight seal is formed between the end portion 14 of the syringe barrel 12 and the inner shield 32 to preserve the sterility of the needle 16. When the rigid needle shield 30 is in place, the end of the needle 16 is received in a distal, closed end of the cavity 34 to block flow from the needle 16. The rigid needle shield 30 can be removed by the application of sufficient force to the casing 36 in the distal direction, to pull the inner shield 32 off the end portion 14 of the syringe barrel 12.

Figure 3:
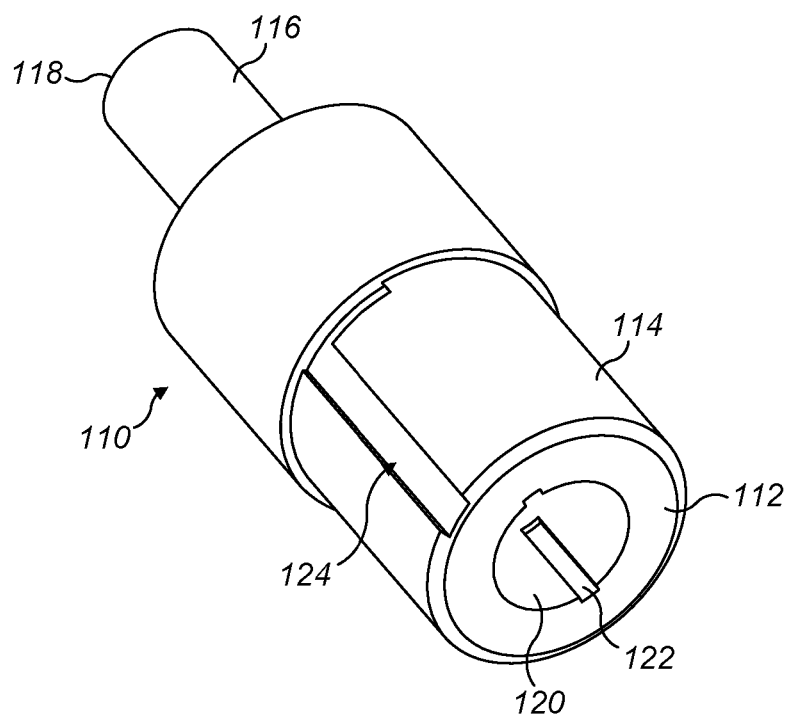
FIG. 3 is an isometric view of a housing component of the injection device of FIG. 1.

The front housing body 110, which is shown in isolation in FIG. 3, comprises a generally tubular body portion 114 and a generally tubular syringe guide 116 that extends proximally from the body portion 114. The body portion 114 has a relatively large diameter, while the syringe guide 116 has a relatively small diameter to receive the barrel 12 of the syringe 10 and to maintain the syringe 10 in an axial orientation in the device 100. As best shown in FIGS. 2(a) and 2(b), when the syringe 10 is mounted in the front housing body 110, the flange 24 of the syringe 10 contacts the distal end 118 of the syringe guide 116 to limit movement of the syringe 10 in the distal direction.

Adjacent to its distal end 112, the body portion 114 of the front housing body 110 has an increased wall thickness to define an elongate passage 120. A pair of longitudinally-extending slots or channels 122 are formed in the wall of the passage 120. A keyway 124, comprising an L-shaped recess or channel, is formed in the outer wall of the front housing body 100. As will be explained below, the channels 122 and the keyway 124 serve to guide parts of the cap assembly 150.

The rear housing body 140 (only part of which is shown in FIGS. 1 to 9) is attached to the front housing body 110 to enclose the distal end of the syringe 10. The plunger 142 is inserted into the barrel 12 of the syringe 10 to cooperate with the stopper 22. The drive mechanism (not shown) is configured to move the plunger 142 from a starting position in the distal direction when the drive mechanism is activated, for example when the user presses a trigger button. The drive mechanism may be of any suitable type. For example, a drive mechanism as described in GB 2516624 can be used.

In FIGS. 2(a) and 2(b), the plunger 142 is shown in its starting position, in which the distal end of the plunger 142 is spaced from the stopper 22 of the syringe 10 by a clearance 144. As is known in the art, the drive mechanism is arranged so that the starting position of the plunger 142 is known relative to the front and rear housing bodies 110, 142.

When the flange 24 of the syringe 10 is against the proximal end 118 of the syringe guide 116, the syringe barrel 12 is in a fixed position relative to the starting position of the plunger 142. However, even with the position of the syringe barrel 12 fixed in this way, the initial position of the stopper 22 of the syringe 10 relative to the starting position of the plunger 142 may still vary between nominally identical syringes, due to dimensional tolerances and inherent variations that arise during the manufacturing process of such syringes.

It can be assumed that, when the syringe 10 is in place in the device, the stopper 22 will initially be positioned within a known tolerance of a nominal position relative to the flange 24 at the proximal end of the syringe barrel 12. The starting position of the plunger 142 is selected such that a minimum clearance 144 will be present between the plunger 142 and the stopper 22, even for cases where the stopper 22 is at its most proximal expected position relative to the nominal position. In this way, during transport and storage of the device before use, the plunger 142 does not apply a force to the stopper 22 that could otherwise cause pressurisation or leakage of medicament.

By way of example, if the allowable tolerance for the initial stopper position is +/−1 mm from a nominal average position, and a minimum clearance 144 of 0.1 mm is desired, then the actual size of the clearance 144 may be anywhere between 0.1 mm and 2.1 mm when the plunger 142 is in its starting position, depending on the particular syringe 10 used in the device 100.

In this example, when the drive mechanism is activated, the plunger 142 is driven to push the stopper 22 to its furthest possible distal position in the syringe barrel 12, which is determined by the position of the shoulder 18. In this way, when activated, the plunger moves to expel substantially all of the medicament 20 in the syringe 10. The quantity of medicament injected is therefore determined by the position of the stopper 22 when the drive mechanism is activated.

To avoid uncertainty in the quantity of medicament delivered, the priming mechanism of the device 100 acts to move the stopper 22 from its initial position to a known, primed position before the drive mechanism is activated. The primed position is at a fixed location relative to the barrel 12 of the syringe 10, and therefore also to the starting position of the plunger 142. Accordingly, once this priming action has taken place, the quantity of medicament injected upon subsequent activation of the drive mechanism is determined by the known primed position of the stopper 22, and is not dependent on the initial position of the stopper 22 after manufacture of the syringe 20.

In this first embodiment, the priming mechanism of the device 100 is incorporated into the cap assembly 150 and the front housing body 110, so that the priming action occurs as the cap assembly 150 is removed from the device 100, as will now be explained.

Figure 4:
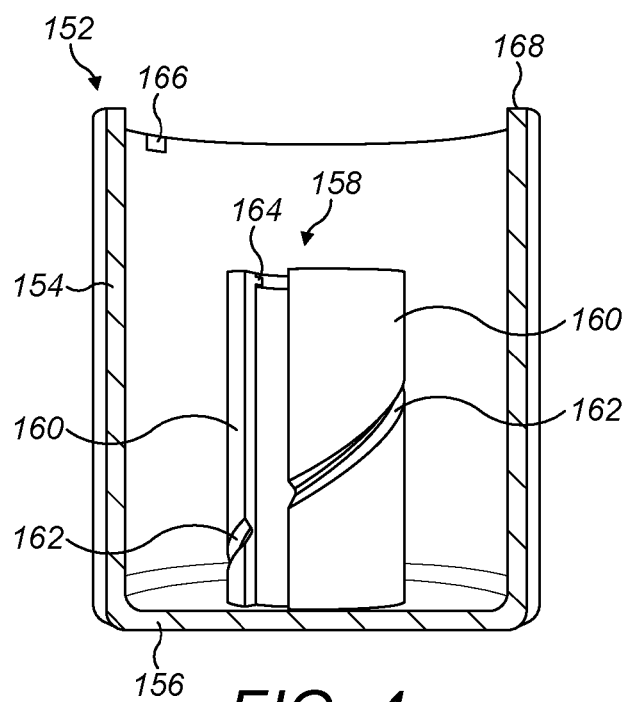
FIG. 4 is a cut-away view of a cap component of the injection device of FIG. 1.

FIG. 4 is a cut-away view of the cap 152 of the cap assembly 150 in isolation. The cap 152 is generally cup-shaped, and comprises an outer wall 154, a distal end face 156, and a shield retainer 158 that extends inwardly from the end face in a proximal direction. In FIG. 4, part of the outer wall 154 is cut away so that the shield retainer 158 is visible. The shield retainer 158 is a tubular formation that is split lengthwise on two opposite sides to form two arcuate arms 160. Each arm 160 has an inclined formation in the form of a helical groove 162 in its outer surface. The grooves 162 are at different axial positions on each arm 160, so that both grooves 162 together describe a single one-turn helix that extends around the shield retainer 158. A clip formation 164 is disposed at the proximal end of each arm 160. The clip formations 164 are ramped on their proximal sides to allow the shield retainer 158 to be pushed over the rigid needle shield 30 during assembly of the device 100.

The cap 152 also includes a locating key 166, in the form of a projection, on the inside surface of the outer wall 154, adjacent to the proximal end 168 of the cap 152.

Figure 5:
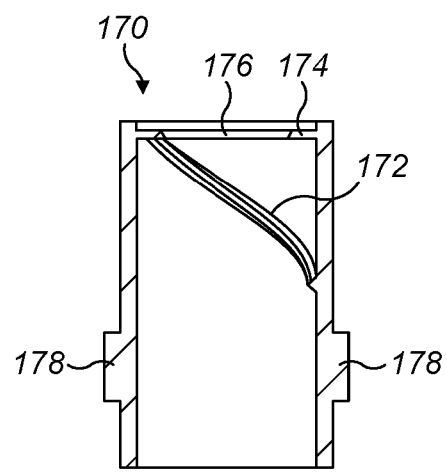
FIG. 5 is a cut-away view of a shuttle member of the injection device of FIG. 1.

Referring to FIG. 5, the shuttle member 170 is generally tubular. A helical projection or rib 172 is disposed on the inner surface of the shuttle member 170. A carrier part in the form of an annular collar 174 is also provided adjacent to the proximal end of the shuttle member 170, to define an aperture 176 with a reduced diameter compared with the internal diameter of the shuttle member 170. Two diametrically-opposed radial projections, referred to hereafter as guide pins 178, are disposed on the outer surface of the shuttle member 170.

The shuttle member 170 is sized to fit concentrically around the shield retainer 158 of the cap 152 to form the cap assembly 150. As best shown in FIGS. 2(a) and 2(b), when the shuttle member 170 is in place, the inclined helical rib 172 of the shuttle member 170 cooperates with the inclined helical grooves 162 in the shield retainer arms 160, so that the shuttle member 170 is retained on the cap 152 by a threaded-type engagement.

When the cap assembly 150 is fitted onto the front housing body 110, the shuttle member 170 and the shield retainer arms 160 extend through the passage 120 in the front housing body 110, between the rigid needle shield 30 and the wall of the passage 120. The clip formations 164 on the proximal ends of the shield retainer arms 160 hook over the proximal end of the rigid needle shield 30 to engage the needle shield 30 with the cap 152. The collar 174 of the shuttle member 170 is positioned between the clip formations 164 and the shoulder 18 of the syringe 10. The diameter of the aperture 176 defined by the collar 174 is larger than the diameter of the end portion 14 of the syringe barrel 12, but smaller than the diameter of the remaining portion of the barrel 12, so that the shoulder 18 cannot pass through the aperture 176.

As can be seen most clearly in FIG. 2(b), the guide pins 178 on the shuttle member 170 engage with the longitudinally-extending channels 122 formed in the wall of the passage 120. The channels 122 constrain movement of the guide pins 178 so that the shuttle member 170 can move only linearly and cannot rotate whilst it is located in the passage 120 of the front housing body 110.

The key 166 of the cap 152 locates in the keyway 124 in the outer wall of the front housing body 110. Cooperation between the key 166 and the keyway 124 serves to provide a bayonet-type fitting for the cap assembly on the device.

Referring additionally to FIG. 6(a), in which the front housing body 110 is visible through the cap 152, when the cap 152 is in a first, initial position relative to the front housing body 110, the key 166 is located in a relatively short, circumferentially-extending part 124a of the keyway 124. The cap 152 cannot be moved axially from this first position. Instead, to allow the cap 152 to be removed, the cap 152 must be turned with respect to the front housing body 110 into a second position, which is shown in FIG. 6(b), to bring the key 166 into alignment with a longitudinally-extending part 124b of the keyway 124. In this way, when in the first position, the cap 152 is locked to the front housing body 110 and cannot be removed from the device 100. To unlock the cap 152, the cap 152 must be turned relative to the front housing body 110 into the second position. The cap 152 can then move distally relative to the front housing body 110 for removal.

By virtue of the engagement of the guide pins 178 of the shuttle member 170 with the slots 122 in the passage 120 of the front housing body 110, the shuttle member 170 cannot turn with the cap 152 when the cap 152 is turned from the first position to the second position. Instead, the shuttle member 170 is forced to move in the proximal direction by the cooperation of the helical grooves 162 of the shield retainer arms 160 with the rib 172 of the shuttle member 170.

Movement of the shuttle member 170 in the proximal direction causes the collar 174 of the shuttle member 170 to press against the shoulder 18 of the syringe barrel 12. As the shuttle member 170 is displaced, the collar 174 carries the syringe barrel 12 in the proximal direction. The clip formations 164 on the shield retainer arms 160 act as holding members to prevent proximal movement of the rigid needle shield 30 relative to the front housing body 110. Therefore, one effect of the proximal movement of the syringe barrel 12 is that the needle 16 is pulled partially away from the rigid needle shield 30. This breaks the seal between the needle 16 and the inner shield 32 and allows medicament 20 to flow out of the syringe 10.

Movement of the syringe barrel 12 in the proximal direction also has the effect of closing the clearance 114 between the stopper 22 and the plunger 142. Once the stopper 22 contacts the plunger 142, the plunger 142, which is held in its starting position by the drive mechanism, prevents further movement of the stopper 22 in the proximal direction. However, the syringe barrel 12 can continue to move and, as a result, the stopper 22 is displaced relative to the syringe barrel 12. This causes medicament 20 to be expressed through the needle 16 and into the cavity 34 of the inner shield 32 of the rigid needle shield 30.

FIGS. 7 and 8 show the device 100 when the cap 152 has been turned into the second position. At this point, further proximal movement of the shuttle member 170 is prevented because the key 166 reaches the end of the circumferentially-extending part 124a of the keyway 124. At this point, the stopper 22 has been moved into a pre-determined, primed position relative to the syringe barrel 12.

The total extent of axial movement of the shuttle member 170 is determined in part by the pitch of the cooperating helical groove 162 and rib 172 of the shield retainer 158 and the shuttle member 170 respectively and in part by the length of the circumferential part 124a of the keyway 124. A desired amount of axial movement of the shuttle member 170, and therefore of the syringe barrel 12, can thus be obtained by appropriate selection of these parameters.

For a given linear displacement of the shuttle member 170, the angle through which the cap 152 must be turned to reach the second position from the first position can be set at a desired value by adjusting the pitch of the helical groove and rib 162, 172. For example, the angle may be set at approximately 45 degrees.

Provided that the total axial movement of the syringe barrel 12 is greater than the sum of the minimum initial clearance 144 between the stopper 22 and the starting position of the plunger 142 and the range of tolerance of the stopper position, the stopper 22 of the syringe 10 will always be moved into the known primed position, irrespective of the initial position of the stopper 22 with respect to the syringe barrel 22.

For example, when the position of the stopper 22 in the syringe 10 has a tolerance of +/−1 mm and the minimum initial clearance 144 between the stopper 22 and the plunger 142 is 0.1 mm, the parameters may be selected to effect a total axial movement of the syringe barrel 12 of 2.2 mm as the cap 152 is turned from its first position to its second position. The axial movement of the shuttle member 170 will be greater than this value by a distance corresponding to any initial clearance between the collar 174 of the shuttle member 170 and the shoulder 18 of the syringe barrel 12.

After priming, the cap assembly 150 can be removed from the device 100 by pulling the cap 152 distally with respect to the front housing body 110. The key 166 passes along the longitudinally-extending part 124b of the keyway 126, allowing the cap 152 to separate from the front housing body 110 as shown in FIG. 9. The rigid needle shield 30, which is retained by the shield retainer arms 160, is removed along with the cap 152. The shuttle member 170, which is engaged with the helical grooves 162 of the shield retainer arms 160, is also removed with the cap 152.

After removal of the cap assembly 150, the needle 16 of the syringe 10 is exposed to allow insertion of the needle 16 into the skin and injection of the medicament 20 upon activation of the drive mechanism of the plunger 142.

The quantity of medicament delivered is determined by the stroke of the stopper 22 as it moves from the primed position to the shoulder 18 at the distal end of the syringe 10. Since the primed position is at a pre-set position with respect to the syringe barrel 12 (and therefore the shoulder 18), the quantity of medicament is not dependent on the initial position of the stopper 22 after manufacture, but can instead be pre-determined by selection of the primed position of the stopper 22.

It will be appreciated that, even if the syringe barrel 12 moves with respect to the front housing body 110 after the cap assembly 150 has been removed, so that a clearance once again appears between the stopper 22 and the plunger 142, this has no effect on the quantity of medicament delivered. In particular, the stroke of the plunger 142 can be set to take the clearance into account.

Advantageously, the priming mechanism of the device 100 is driven by the unlocking action of turning the cap 152 from the first position to the second position. In this way, the cap 152 acts as an operating member of the priming mechanism. Since the cap 152 must be unlocked and removed before the device can be used, no additional action is required on the part of the user to prime the device. Furthermore, priming occurs automatically as a precursor to removal of the cap before use of the device 100.

In the above-described embodiment of the invention, the rigid needle shield 30 is held by the clip formations 164 on the shield retainer 158 of the cap 152. When the cap 152 is turned from the first position to the second position to prime the device, the shield retainer 152 also turns, so that a turning moment is applied to the rigid needle shield 30 by way of the clip formations 164.

It is, however, desirable to avoid rotation of the rigid needle shield 30 with respect to the needle 16 and the syringe barrel 12, since otherwise fragments of the elastomeric inner shield 32 could be cut by the needle 16 and cause blockages (known in the art as needle coring). Provided that the turning moment applied to the rigid needle shield 30 by the clip formations 164 is not sufficient to overcome friction between the inner shield 32 and the end portion 14 of the syringe barrel 12, the rigid needle shield 30 will not rotate with respect to the syringe barrel 12 and coring problems will be avoided.

To reduce further the possibility that the rigid needle shield will rotate during priming of the device, in other embodiments of the invention, means for reducing friction between the shield retainer and the rigid needle shield are provided, to reduce the turning moment applied by the shield retainer to the rigid needle shield during priming of the device.

By way of example, FIGS. 10(a) and 10(b) illustrate two possible ways of reducing friction between the shield retainer 158 and the rigid needle shield 30 in variants of the device 100 of the first embodiment of the invention. In these cases, slip means are provided to reduce friction between the clip formations 164 and the shield 30.

In a first variant of the device, illustrated in FIG. 10(a), the slip means comprises a low-friction washer 165 provided between the cover 36 of the rigid needle shield 30 and the clip formations 164 of the shield retainer arms 160 (only one of which is shown in FIG. 10(a)). The washer 165 may, for example, be of PTFE or a similar low-friction material. In another variant (not illustrated), the cover of the rigid needle shield and/or the clip formations are provided with a low-friction coating, such as a PTFE coating.

In a second variant, illustrated in FIG. 10(b), slip means in the form of rounded projections 164a are formed on the distal sides of the clip formations 164, such that the cover 36 of the rigid needle 30 shield bears against the rounded projections 164a. In this way, the contact area between the rounded projections 164a and the cover 36 of the rigid needle shield 30 is reduced, which in turn reduces the turning moment applied to the rigid needle shield 30 when the device is primed.

The possibility of needle coring can also be reduced by providing means to increase the resistance of the rigid needle shield to turning. For example, features may be added to engage the rigid needle shield with any part of the device that does not turn when the device is primed. For example, in a third variant of the device 100, illustrated in FIG. 10(c), a projection 170a on the inner surface of the shuttle member 170 extends through a slot 160a in the shield retainer arm 160 (although the projection 170a could instead extend through the gap between the shield retainer arms 160). The projection 170a bears against the cover 36 of the rigid needle shield 30. Because the shuttle member 170 does not turn when the device is primed, the projection 170a acts to increase the resistance of the rigid needle shield 30 to turning during priming.

A still further approach is shown in FIG. 11, which illustrates an injection device 200 according to a second embodiment of the invention. In this second embodiment, the cap 252, which is shown in a cut-away view in FIG. 12, differs from the cap 152 of the device 100 described above with reference to FIGS. 1 to 9.

In particular, the tubular shield retainer 258 of the cap 252 of the device 200 is split into an upper portion 258a and a lower portion 258b. As best seen in FIG. 11, the distal end of the upper portion 258a has an annular clip formation 259a that engages with a complementary clip formation 259b on the proximal end of the lower portion 258b. The lower portion 258b is formed as part of the cap 252.

The upper portion 258a of the shield retainer 258 is divided to form two arms 260 that engage with the rigid needle shield 30 by way of clip formations 264 provided at the distal ends of the arms 260. Only the lower portion 258*b* of the shield retainer 258 carries a helical groove 262 for engagement with the corresponding rib 272 of the shuttle member 270. In this embodiment, the rib 272 of the shuttle member 270 is present only on the distal half of the shuttle member 270, so that the rib 272 does not foul the upper portion 258*a* of the shield retainer 258.

The cooperating clip formations 259*a*, 259*b* allow the upper portion 258*a* of the shield retainer 258 to rotate independently with respect to the lower portion 258*b*. Accordingly, with this arrangement, the upper portion 258*a* of the shield retainer 258 does not turn when the cap 252 is moved from the first position to the second position to move the carrier part 272 of the shuttle member 270 into engagement with the syringe body 12 to prime the device 200. Accordingly, no turning moment is applied to the rigid needle shield 30 during priming. When the cap 252 is subsequently removed from the device 200, the upper portion 258*a* is removed along with the lower portion 258*b* so that, as in the first embodiment, the rigid needle shield 30 is removed along with the cap 252.

FIGS. 13 and 14 show cross-sectional views of an injection device 300 according to a third embodiment of the invention. In this case, the injection device 300 comprises an auto-injector, in which, upon activation, the drive mechanism causes the needle 16 of the syringe 10 to advance into the skin before injection of the medicament 20.

The device 300 includes a front housing body 310, a rear housing body 340 that clips to a proximal end of the front housing body 310, and a cap assembly 350 that closes a distal end 312 of the front housing body 310. The front housing body 310 houses the syringe 10.

The syringe 10 is received in a syringe guide 316. Unlike in the devices 100, 200 of the first and second embodiments of the invention, in this third embodiment the syringe guide 316 comprises a carrier that is slidable within the front housing body 310 to allow displacement of the syringe 10 with respect to the front housing body 310.

A rubber damping sleeve 319 is provided between the flange 24 of the syringe 10 and the distal end 318 of the syringe guide 316. At its distal end, the syringe guide 316 is provided with an annular clip formation 311 on its outer surface. As best shown in FIG. 13(*b*), two support arms 313 extend from the inner wall of the front housing body 310 to embrace the syringe guide 316 therebetween. The clip formation 311 on the syringe guide 316 engages with stops 315 at the proximal ends of the support arms 313 to limit movement of the syringe guide 316 in the proximal direction.

The syringe guide 316 is biased in the proximal direction by a biasing spring 317. One end of the biasing spring 317 acts on a shoulder 321 in the bore of the syringe guide 316, while the other end of the biasing spring 317 acts on a collar 323 of a tubular sleeve component 325 that receives a distal part of the syringe 10.

An annular rib 327 on the sleeve component 325 abuts a stop 329 formed on the inner surface of the front housing body 310, as shown in FIG. 13(*a*), to limit movement of the sleeve component 325 in the distal direction. In the initial state of the device 300, as shown in FIGS. 13(*a*) and 13(*b*), the syringe 10 is positioned so that the needle 16 is retracted within the front housing body 310 (i.e. the tip of the needle 16 is located proximally with respect to the distal end 312 of the front housing body 310).

As in the previous embodiments of the invention, a priming mechanism of the device 300 is provided by cooperation between a cap 352 and a shuttle member 370 of the cap assembly 350.

Referring additionally to FIG. 14, which is an isometric view of the shuttle member 370, the shuttle member 370 is generally tubular and is arranged to fit over the proximal end of a shield retainer 358 of the cap 352, which is illustrated in FIG. 15.

As in the first and second embodiments described above, in this third embodiment the shield retainer 358 of the cap 352 comprises a pair of proximally-extending arms 360, each of which is provided with a clip formation 364 adjacent to its proximal end to grip the rigid needle shield 30 when the cap 352 is in place on the front housing body 310. However, instead of a helical groove or thread formation, in this third embodiment the inclined formation comprises a ramped projection 362 provided on the proximal end of each arm 360 for cooperation with the shuttle member 370.

To this end, the shuttle member 370 comprises a pair of projections in the form of arcuate ribs 372 on its inner surface. Only one of the ribs 372 can be seen in FIG. 14. When the shuttle member 370 is in place on the proximal end of the shield retainer 358, the ramped projections 362 locate in the spaces between the ribs 372. A central portion of each rib 372 is extended radially to form a carrier part or tab 374 for engagement with the shoulder 18 of the syringe barrel 12, as will be explained below.

The shuttle member 370 is provided with guide ribs 378 that locate in channels (not shown) in the sleeve component 323, so that rotation of the shuttle member 370 with respect to the sleeve component 323 and the front housing body 310 is not possible.

The cap 352 includes a key 366 for cooperation with a keyway (not shown) in the front housing body. As in the previously-described embodiments, the keyway guides movement of the cap 352 so that the cap 352 must be turned from a first position to a second position before it can be removed from the device 300.

The drive mechanism for the plunger 342 is housed in the rear housing body 340 of the device 300. The plunger 342 carries a spring collar 343, which is disposed adjacent to the distal end of the rear housing body 340. One end of a drive spring 344 is seated on the spring collar 343, and the other end of the drive spring 344 acts against a spring seat 345 provided at the proximal end of the rear housing body 340. In this way, the drive spring 344 biases the plunger 342 in the distal direction, towards the stopper 22 of the syringe 10.

As best shown in FIG. 13(*b*), a pair of latching arms 346 are formed at the proximal end of the plunger 342. Each latching arm 346 has a head portion 347 with a ramped proximal face and a distal face that is substantially perpendicular to the axis of the plunger 342. The head portions 347 engage with a bridge part 341 of the rear housing body 340, so that the latching arms 344 clip on to the bridge part 341 to lock the plunger 342 in its starting position.

A trigger button 348 is retained in the proximal end of the rear housing body 340. The trigger button includes a tubular skirt 349, which extends distally towards the bridge part 341 of the housing body.

To use the device 300, the cap 352 is first unlocked by turning the cap 352 with respect to the housing body 310 from the first position to the second position. During turning movement of the cap 352, the ramped projections 362 of the shield retainer 358 act upon end surfaces of the arcuate ribs 372 of the shuttle member 370 to move the shuttle member 370 in the proximal direction with respect to the front housing body 310.

As best seen in FIG. 13(a), when the shuttle member 370 moves in the proximal direction, the tabs 374 provided on the arcuate ribs 372 of the shuttle member 370 engage with the shoulder 18 of the syringe barrel 12, to move the syringe 10 in the proximal direction relative to the front housing body 310. As in the previously-described embodiments of the invention, this results in the stopper 22 of the syringe 10 being displaced into a pre-determined primed position by the plunger 342, which is held in its starting position by the drive mechanism.

The cap 352 can then pulled distally off the front housing body 310. The rigid needle shield 30 is removed along with the cap 352. However, in this embodiment, the shuttle member 370 is not removed with the cap 352, but is instead held captive within the front housing body 310. When the cap 352 is withdrawn, the shuttle member 370 engages with inwardly-extending ribs 331 formed on the inner surface of the sleeve component 325 (as shown most clearly in FIG. 13(b)). The shuttle member 370 cannot pass the ribs 331, and is therefore retained in the front housing body 310. In this way, if the syringe 10 should break during activation of the device so that part of the syringe body 12 becomes detached from the flange 24, the tabs 374 of the captive shuttle member 370 catch the shoulder 18 of the syringe 10 and prevent the syringe body 12 from being released from the device 300.

After removal of the cap 352, the device 300 is positioned with the distal end 312 of the front housing body 310 against the skin, and the trigger button 348 is depressed to activate the drive mechanism. Depression of the trigger button 348 causes the skirt 349 of the trigger button 348 to bear against the ramped proximal faces of the head portions 347 of the latching arms 346. In turn, this causes the latching arms 346 to splay apart, to allow the head portions 347 to pass the bridge part 341, releasing the plunger 342 for movement in the distal direction under the force of the drive spring 344.

Once released, the plunger 342 moves distally to engage with the stopper 22 of the syringe 10. This first causes the syringe 10 and the syringe guide 316 to move distally with respect to the front housing body 310, moving the needle 16 of the syringe 10 out of the distal end of the front housing body 310 and into the skin. Then, continued movement of the plunger 342 forces the stopper 22 distally along the barrel 12 of the syringe 12, injecting the medicament 20. Because the stopper 22 is moved into the primed position before activation of the device mechanism, the amount of medicament delivered is accurately known.

In the above-described embodiments, a shuttle member is used to convert turning movement of the cap to linear movement of the syringe. However, various alternative ways of achieving linear movement of the syringe during priming are possible.

For example, an injection device 400 according to a fourth embodiment of the invention is shown in FIGS. 16(a) and 16(b). The injection device 400 is generally similar to the first embodiment of the invention described above with reference to FIGS. 1 to 9 except in that, in this fourth embodiment, the priming mechanism does not include a shuttle member. Instead, the cap 452 incorporates a carrier part to move the syringe, and the front housing body 410 provides holding members to prevent proximal movement of the shield 30.

Referring first to FIG. 16(a), the front housing body 410 includes a syringe guide 416 that supports the barrel 12 of the syringe 10, and a passage 420 that receives the rigid needle shield 30 of the syringe 10. A pair of proximally-extending arms 421 are disposed at the periphery of the passage 420 on its proximal side. Each arm 421 supports an inwardly-projecting finger 423. When the syringe 10 is in place, the fingers 423 project into the space between the rigid needle shield 30 and the shoulder 18 of the syringe barrel 12.

Referring to FIG. 16(b), the cap 452 includes a shield retainer 458 having a pair of proximally-projecting arms 460. The proximal end of each arm 460 is provided with a clip formation 464 to engage with the proximal end of the rigid needle shield 30. The clip formations 464 are also arranged to cooperate with the shoulder 18 of the syringe barrel 12, thereby acting as carrier parts.

In use of the device 400, the cap 452 is first moved in the proximal direction with respect to the front housing body 410 from an initial, first position to a second position. During proximal movement of the cap 452, the clip formations 464 push against the shoulder 18 of the syringe barrel 12. The clip formations 464 therefore act as carrier parts to carry the syringe 10 in the proximal direction. At the same time, the fingers 423 act as holding members to hold the rigid needle shield 30, so as to prevent proximal movement of the rigid needle shield 30 relative to the front housing body 410. Accordingly, the syringe 10 is partially withdrawn from the rigid needle shield 30, allowing medicament 20 to flow out of the needle 16.

As in previous embodiments of the invention, this proximal movement of the syringe 10 causes the stopper 22 to be displaced from its initial position into a known primed position, and the medicament 20 that is displaced as a result flows out of the needle 16 into the rigid needle shield 30.

In this example, the second position of the cap 452 is reached when the proximal end 455 of the wall 454 of the cap 452 contacts a step 413 formed on the outer surface of the front housing body 410.

The cap 452 can then be removed by pulling the cap 452 in the distal direction with respect to the front housing body 410. The rigid needle shield 30 is retained by the shield retainer arms 460 and is therefore removed along with the cap 452. The device 400 is then ready for injection, as described with reference to the first and second embodiments of the invention above.

Although not shown in FIGS. 16(a) and 16(b), the cap 452 may be guided for linear movement with respect to the front housing body 410. A locking mechanism may be provided, so that the cap 452 can only be removed from the front housing body 410 once it has been moved proximally from the first position to the second position.

For example, the cap 452 and the front housing body 410 could be engaged by way of a J-shaped keyway, in which case simultaneous proximal and turning movement of the cap 452 is required prior to withdrawal of the cap 452 in the distal direction. By way of illustration, FIG. 17(a) shows part of the front housing body 410 of a variant of the device of FIG. 16, in which a J-shaped keyway 424 is provided. The keyway 424 is arranged for engagement with a corresponding projection or key (not shown) provided on the cap 452.

The keyway 424 includes a first inclined part 424a and a second inclined part 424b. The inclined parts 424a, 424b of the keyway 424 extend helically and in opposite senses around respective segments of the front housing body 410, so that the proximal end of the first inclined part 424a meets the proximal end of the second inclined part 424b. The distal end of the second inclined part 424b opens onto the distal end face of the front housing body 410.

Initially, when the cap is in the first position, the key of the cap 452 is located at the distal end of the first inclined part 424a. A detent 425 is provided in the first inclined part 424a of the keyway 424 to provide resistance to accidental movement of the cap 452 away from the first position. The detent 425 is sized so that application of a small user force to the cap 452 is sufficient to allow the key to move away from the distal end of the first inclined part 424a of the keyway 424.

In this variant, the user removes the cap 452 by turning the cap 452 with respect to the front housing body 410. The first inclined part 424a of the keyway 424 is angled so that the cap 452 is guided to move in the proximal direction as it turns, with the key travelling along the first inclined part 424a of the keyway 424. As described above, as the cap 452 moves in the proximal direction, the clip formations 464 (see FIG. 16) carry the syringe barrel 12 in the proximal direction. The fingers 423 block movement of the needle shield 30 in the proximal direction, so that the needle shield 30 is released from the syringe 10, and the stopper 22 of the syringe 10 is pressed against the plunger 142 into the primed position.

The cap 452 reaches its second position, at the end of the priming movement, when the key reaches the proximal end of the first inclined part 424a of the keyway 424.

Upon further turning movement of the cap 452, the key is guided along the second inclined part 424b of the keyway 424. The second inclined part 424b of the keyway 424 is angled so that the cap 452 is driven to move in the distal direction, causing the clip formations 464 to engage with the needle shield 30. The cap 452, together with the needle shield 30, can be removed from the device when the key emerges from the distal end of the second inclined part 424b of the keyway 424.

In the above-described examples, release of the needle shield from the syringe is achieved by blocking the proximal movement of the needle shield as the syringe body is driven proximally by the priming mechanism. It should, however, be understood that alternative ways of releasing the needle shield are possible.

For example, in an alternative arrangement, release of the needle shield can be achieved by initially applying a distal force to the needle shield whilst blocking distal movement of the syringe body. After the seal between the needle shield and the syringe has been released, the syringe body can then be moved proximally to displace the stopper to the primed position.

By way of illustration, FIG. 17(b) shows part of the front housing body 410 of a further variant of the device of FIG. 16. In this case, the front housing body 410 is provided with a keyway 524 that is generally S-shaped.

The keyway 524 thus includes a first inclined part 524a, a second inclined part 524b, and a third inclined part 524c. The first, second and third inclined parts 524a, 524b. 524c of the keyway 524 extend helically and in alternating senses around respective segments of the front housing body 410. The distal end of the first inclined part 524a connects with the distal end of the second inclined part 524b, and the proximal end of the second inclined part 524b connects with the proximal end of the third inclined part 524c. The distal end of the third inclined part 524c opens onto the distal end face of the front housing body 410.

In this variant, when the cap 452 is in the first position, the key is located at the proximal end of the first inclined part 524a of the keyway 524. A detent 525 is provided to guard against unintentional movement of the cap 452.

In use, when the cap 452 is turned by the user, the key first moves along the first inclined part 524a to guide movement of the cap 452 from the first position to an intermediate position in which the key is disposed at the distal end of the first inclined part 524a. Interaction between the key and the first inclined part 524a causes distal movement of the cap 452 with respect to the front housing body 410. The clip formations 464 (see FIG. 16) therefore engage with the needle shield 30, and the fingers 423 block distal movement of the syringe body 12, the needle shield 30 is released from the syringe 10.

Upon continued turning movement of the cap 452, the key moves along the second inclined part 524b of the keyway 524, guiding the cap 452 from the intermediate position to the second position. Interaction between the key and the second inclined part 524b causes proximal movement of the cap 452.

The keyway 524 is arranged so that the second position is disposed proximally with respect to the first position, so that there is a net proximal movement of the cap 452 as the cap 452 is moved from the first position to the second position by way of the intermediate position. Accordingly, the clip formations 464 of the cap 452 engage with the syringe body 12 to move the syringe body 12, thereby to cause displacement of the stopper 22 to the primed position. Subsequently, the cap 452, along with the needle shield 30, can turned further to guide the key along the third inclined part 524c of the keyway 524 until the key disengages from the keyway 524, releasing the cap 452 from the device.

In this variant, the fingers 423 act to block distal movement of the syringe body 12 during distal movement of the cap 452. Distal movement of the syringe body 12 can also be blocked by abutment of the flange 24 against the proximal end of the syringe guide 416, or against another suitable component. In such cases, the fingers 423 or other holding members may be omitted.

In the variant of FIG. 17(b), the cap moves distally as it is turned from the first position to the intermediate position, then proximally as it is turned from the intermediate position to the second position, and then distally once more as it is removed from the device. In some applications, it may be desirable to avoid distal and proximal movement of the cap as it is turned from the first position to the second position. This can be achieved, for example, by including a cylindrical outer cap sleeve that can be turned by the user. In this arrangement, the cap is coupled to the cap sleeve so that turning movement of the cap sleeve causes turning movement of the cap, but the cap is slidable with respect to the cap to allow displacement of the cap through a suitable distance in the distal and proximal directions as the cap is moved from the first position to the second position.

Similarly, the first, second and third embodiments described above can be modified so that, upon an initial movement of the cap from the first position to an intermediate position, the shuttle member is driven to move in the distal direction to release the shield from the syringe, and then upon further movement of the cap from the intermediate position to the second position, the shuttle member is driven to move in the proximal direction to carry the syringe body proximally to move the stopper to the primed position.

Any suitable means for achieving the distal and proximal movement of the shuttle member may be provided. For example, a similar key and keyway arrangement to that described with reference to FIG. 17(b) could be provided to couple the shuttle member to the cap and to drive the distal and proximal movement of the shuttle member with respect to the cap upon a turning movement of the cap, in place of the helical projection and groove or ramp formation arrangements described above.

In another arrangement, the cap may be coupled to the housing in such a way that initial movement of the cap from the first position to the intermediate position includes a distal movement of the cap with respect to the housing, and so that further movement of the cap from the intermediate position to the second position includes a turning movement. The shuttle member, in turn, may be coupled to the cap so that the shuttle member is carried distally by the operating member during the initial distal movement of the cap, and so that an inclined formation (such as a helical projection and groove, or a ramp formation) drives proximal movement of the shuttle member during the further turning movement of the cap.

In these variants, the priming mechanism includes one or more carrier parts provided on the shuttle member or the cap that cooperate with both the needle shield and the syringe body. However, it is also conceivable that separate shield engagement parts could be provided for cooperation with the needle shield to move the needle shield in the distal direction with respect to the housing, in which case the carrier parts may be arranged to cooperate only with the syringe body. The shield engagement parts and the carrier parts may be provided on the same component of the device (such as on a shuttle member or the cap), or on different components.

As noted above, providing a priming mechanism in accordance with the present invention improves the accuracy of the quantity of medicament delivered and reduces variability between nominally identical devices. This is of particular benefit when the volume of medicament to be delivered in a dose is small. Accordingly, it may be desirable to employ the present invention in injection devices that are adapted for the delivery of small doses of medicament.

One convenient way of providing smaller volumes of medicament for injection is only partially to fill the barrel 12 of the syringe 10, so that the stopper 22 of the syringe 10 is closer to the distal end of the syringe 10 than for a fully-filled syringe. The injection devices described with reference to FIGS. 1 to 17 can be readily adapted for use with partially-filled syringes by the use of plungers with appropriate lengths.

Alternatively, an injection device according to the invention could be fitted with a plunger with adjustable length. This has the advantage of allowing a common device design to be used for different doses of a medicament, so that it is not necessary to manufacture plungers of several different lengths.

FIGS. 18(*a*) and 18(*b*) show one example of an adjustable-length plunger 542 that is suitable for use with the devices of the present invention. The plunger 542 is of two-part construction and comprises a proximal plunger holder part 543 and a distal plunger rod part 545, which are shown separately in FIG. 18(*a*). The plunger rod 545 is externally ribbed, and the holder 543 is provided with channel 547 to accept the rod 545, as shown in FIG. 18(*b*). The walls of the channel 547 are grooved to engage with the ribs of the rod 545. The length of the plunger 542 can be adjusted to suit a particular application by setting the rod 545 into the channel 547 of the holder 543 at an appropriate position to leave a desired length of the rod 545 extending beyond the end of the holder 543. The engagement of the ribs of the rod 545 with the grooves of the channel 547 prevents subsequent changes in the length of the plunger 542. The holder 543 includes a suitable fitting (not shown) at its proximal end to connect the plunger 542 to the drive mechanism of the device.

FIGS. 19(*a*) and 19(*b*) show another example of an adjustable-length plunger 642 of two-part construction. Referring first to FIG. 19(*a*), in this example the plunger rod 645 includes a pair of latching pins 646 disposed on opposite sides of the rod 645. The plunger holder 643 is tubular to define a bore 547 for receiving the rod 645. A plurality of holes 649 extend through the wall of the plunger holder 643. The holes 649 are arranged in pairs on opposite sides of the holder 643.

A longitudinally-extending slot 648 extends through the rod 645 between the latching pins 646. The slot 648 allows the latching pins 646 to move towards one another across the diameter of the rod 645 when the rod 645 is inserted in the bore 647 of the holder 643, as shown in FIG. 19(*b*). The latching pins 646 engage with one pair of holes 649 to hold the rod 645 in place with respect to the holder 643. In the illustrated example, four pairs of holes 649 are provided, so that the length of the plunger 642 can be set to one of four lengths, although fewer or more pairs of holes could be provided.

Another plunger arrangement 742 is shown in FIG. 20, which illustrates part of an injection device 700 according to a fifth embodiment of the invention. The device 700 is similar to the device of the third embodiment described above with reference to FIGS. 13(*a*) and 13(*b*), and so only the differences will be described in detail.

Unlike in the previously-described embodiments, in which the stopper of the syringe is pushed against the plunger to prime the device, in the device 700 of FIG. 20 includes a separate priming member 780 that cooperates with the stopper during priming.

The priming member 780 comprises a pin or rod that extends through an axial bore 747 formed in the plunger 742. A proximal end 782 of the priming member 780 is seated in a socket 784 provided on the distal side of the bridge part 741 of the rear housing body 740. At its distal end, the priming member 780 terminates in a contact disc 786. The distal end face 788 of the plunger 742 includes a recess 790 to accommodate the contact disc 786 when the plunger 742 moves in the distal direction, as will be explained below.

The plunger 742 is provided with a bell-shaped spring seat 743. The spring seat 743 supports the distal end of the drive spring 744. As described above with reference to FIG. 13(*b*), the plunger 742 is clipped to the bridge part 741 of the rear housing body 740 by latching arms (not shown in FIG. 20) to latch the plunger 742 in its starting position.

When the plunger 742 is in its starting position, as shown in FIG. 20, the contact disc 786 of the priming member 780 is spaced distally from the distal end 788 of the plunger 747. Accordingly, when the priming mechanism (not shown in FIG. 20) is used to move the syringe barrel 12 in the proximal direction with respect to the plunger 742, the stopper 22 comes into contact with the contact disc 786 of the priming member 780. Proximal movement of the priming member 780 is blocked by the bridge part 741 of the rear housing body 740, so continued movement of the syringe barrel 12 in the proximal direction causes the priming member 780 to displace the stopper 22 into its primed position.

After priming, the drive mechanism is activated to unlatch the plunger 742 from the bridge portion 741 of the rear housing body 740, so that the plunger 742 moves in the distal direction. The plunger 742 is movable with respect to the priming member 780 so that, initially, the contact disc 786 enters the recess 790 in the distal end 788 of the plunger 742 to couple the priming member 780 to the plunger 742. Continued movement of the plunger 742 causes the proximal end 782 of the priming member 780 to be pulled out of the socket 784, so that the priming member 780 detaches from the rear housing body 740.

The plunger 742 and the priming member 780 then travel distally together, and the distal end face 788 of the plunger 742 contacts the stopper 22 to expel medicament from the syringe 10.

Because the stopper 22 is pushed against the priming member 780 and not the plunger 742 during priming, the length of the priming member 780 can be selected as appropriate for a given fill volume of the syringe 10, allowing the same length of plunger 742 to be used for any fill volume. Furthermore, it is not necessary to adjust the stroke of the plunger to suit different fill volumes. Also, because the priming member 780 is a single component that abuts the rear housing body 740, dimensional tolerances are low and the position of the contact disc 786 of the priming member 780 relative to the rear housing body 740 can be selected with a high degree of accuracy. In this way, variations in the position of the stopper 22 after priming are further reduced.

Various modifications of the arrangement of FIG. 20 are possible. For example, the socket in the bridge portion and the proximal end of the priming member can be arranged to engage in any suitable way. For example, the socket and/or the priming member may have a frustoconical shape so that the priming member wedges in the socket. The priming member may have a blind bore in its proximal end to accept a pin of the socket.

In another variation, the plunger does not couple with the priming member. Instead, the plunger is able to pass the priming member, which remains attached to the bridge portion of the rear housing body.

In a further variation, the distal end of the priming member continues to protrude from the distal end of the plunger after the priming member has been pulled out of the socket. In this case, the distal end of the priming member contacts and pushes the stopper to expel medicament from the syringe.

Various other modifications of the examples described above are possible. For example, in the above-described embodiments, movement of the cap of the device is used to drive the priming action of the device. However, a different operating member could be used. For instance, the priming mechanism could be operated by a separate priming collar that can be turned with respect to the housing body of the device to drive linear movement of a shuttle member. In another example, the operating member could be a button, slider or other component configured for turning and/or linear movement with respect to the housing body. In such cases, the operating member may also serve to unlock the cap to ensure that priming takes place before injection, but arrangements in which the operating member is independent of the cap are also possible.

In the above-described embodiments, the priming mechanism moves the syringe proximally with respect to the housing body while the plunger is fixed in its staring position, so that the syringe moves proximally relative to the plunger. However, it is conceivable that the plunger could be moved distally with respect to the housing body to achieve the same relative movement between the syringe and the plunger.

Various features of the above-described examples could be substituted with structurally and/or functionally equivalent features. In particular, where parts are configured to cooperate by way of a rib, pin, key or other projection in engagement with a slot, channel, keyway or other recess, the projection and the recess could be provided on either part. By way of example, in the first and second embodiments of the invention, the helical rib may be provided on the shield retainer, with the corresponding groove being formed on the shuttle member. Guide pins could be provided on the passage in the front housing body for engagement with recesses in the shuttle member. Similarly, guiding of the cap on the front housing body could be achieved by way of a key provided on the front housing body that engages with a keyway provided on the cap.

When movement of the operating member is non-linear, any suitable mechanism for converting movement of the operating member to linear movement of the syringe body could be used. Examples of possible mechanisms include threaded arrangements, cam and follower arrangements and so on.

It will also be understood that a device according to the invention may include additional or alternative housing parts, and other parts such as casing parts, interlock parts, shield parts for shrouding the needle after injection, and so on. The priming mechanism could make appropriate use of any suitable combination of such parts.

The drive mechanism described above with respect to the third embodiment of the invention could be used to drive the plunger of the devices of the first, second and fourth embodiments of the invention, although any suitable drive mechanism could be used. The first, second and fourth embodiments could be modified to function as auto-injectors. Similarly, the third embodiment could be modified for manual needle insertion.

In the above-described examples, the plunger is driven to push the stopper to its furthest possible distal position in the syringe barrel to expel substantially all of the medicament in the syringe. However, the drive mechanism may be arranged to move the plunger from its starting position to a second position to move the stopper only partially along the syringe barrel, so as to expel only a pre-set portion of the total volume of medicament in the syringe. Furthermore, the drive mechanism may be arranged to advance the plunger from the second position to one or more further positions, for delivery of subsequent doses from the same syringe. With a suitable drive mechanism, the second and further positions may be adjustable and/or user selectable.

More generally, the invention can be used in injection devices in which the needle of the syringe is inserted into the skin manually, as in the first, second and fourth embodiments described above, or in auto-injectors in which needle insertion is automatic. Needle retraction after injection may also be automatically driven by the injection device. The invention is not limited to use with Hypak-type syringes with a rigid needle shield of the type described, but could be used with any similar syringe, with any type of needle shield. It is also conceivable that the invention could be used with other types of pre-filled medicament container, such as cartridges that are designed for use with disposable needles.

Further modifications and variations not explicitly described above are also possible without departing from the scope of the invention as defined in the appended claims.

The invention claimed is:

1. An injection device for injection of a medicament from a pre-filled container having a container body for containing the medicament, a needle disposed at a distal end of the container body, a removable needle shield and a stopper for expelling medicament from the container, the device comprising:
- a housing for housing the container;
- a plunger for driving the stopper of the container in a distal direction to expel the medicament; and
- a priming mechanism having an operating member which is movable with respect to the housing;
- wherein the priming mechanism is arranged to release the needle shield from the needle and to move the container body in a proximal direction with respect to the plunger upon movement of the operating member from a first position to a second position during an operating sequence of the device.

2. The injection device according to claim 1, wherein the priming mechanism is arranged to prevent movement of the needle shield in the proximal direction when the container body is moved in the proximal direction with respect to the plunger.

3. The injection device according to claim 2, wherein the device comprises at least one holding member for blocking movement of the needle shield in the proximal direction when the operating member is moved from the first position to the second position.

4. The injection device according to claim 3, wherein the or each holding member is attached to the operating member.

5. The injection device according to claim 4, wherein the or each holding member is slidably attached to the operating member to permit turning movement of the operating member with respect to the needle shield.

6. The injection device according to claim 3, wherein the or each holding member is attached to the housing.

7. The injection device according to claim 3, comprising slip means for reducing friction between the or each holding member and the needle shield.

8. The injection device according to claim 1, wherein the priming mechanism is arranged to move the needle shield in the distal direction with respect to the housing, thereby to release the needle shield from the needle.

9. The injection device according to claim 8, wherein the priming mechanism is arranged to move the needle shield in the distal direction with respect to the housing before moving the container body in the proximal direction with respect to the plunger.

10. The injection device according to claim 8, wherein the priming mechanism is arranged to move the needle shield in the distal direction with respect to the housing upon movement of the operating member from the first position to an intermediate position, and to move the container body in the proximal direction with respect to the plunger upon movement of the operating member from the intermediate position to the second position.

11. The injection device according to claim 1, comprising a resistance member arranged to prevent turning movement of the needle shield with respect to the container body.

12. The An injection device according to claim 1, wherein the operating member comprises a removable cap for closing a distal end of the housing.

13. The injection device according to claim 12, wherein, when the cap is in the first position, the cap is locked against removal from the housing and, when the cap is in the second position, the cap is unlocked for removal from the housing.

14. The injection device according to claim 12, wherein the cap comprises a shield retainer to retain the shield in the cap when the cap is removed.

15. The injection device according to claim 14, wherein the shield retainer comprises a holding member for blocking movement of the needle shield in the proximal direction.

16. The injection device according to claim 1, comprising a carrier part arranged to cooperate with the container body to move the container body in the proximal direction with respect to the plunger.

17. The injection device according to claim 16, wherein the carrier part is arranged to cooperate with a shoulder of the container body.

18. The injection device according to claim 16, wherein the carrier part is arranged to cooperate with the needle shield to release the needle shield from the needle.

19. The injection device according to claim 16, further comprising a shield retainer to retain the shield in the cap when the cap is removed, wherein the shield retainer comprises the carrier part.

20. The injection device according to claim 1, wherein movement of the operating member from the first position to the second position comprises a turning movement.

21. The injection device according to claim 20, wherein the priming mechanism comprises a shuttle member arranged to cooperate with the operating member and the container body.

22. The injection device according to claim 21, wherein the shuttle member is generally tubular for cooperation with a cylindrical or part-cylindrical surface of the operating member.

23. The injection device according to claim 21, comprising an inclined formation for moving the shuttle member in the proximal direction upon movement of the operating member from the first position to the second position.

24. The injection device according to claim 23, wherein the inclined formation comprises a helical groove or projection on the operating member for cooperation with a corresponding projection or groove of the shuttle member.

25. The injection device according to claim 23, wherein the inclined formation comprises a ramp for cooperation with a surface of the shuttle member.

26. The injection device according to claim 21, further comprising a carrier part arranged to cooperate with the container body to move the container body in the proximal direction with respect to the plunger, wherein the shuttle member comprises the carrier part.

27. The injection device according to claim 21, comprising guide means for preventing rotation of the shuttle member with respect to the housing when the operating member is moved from the first position to the second position.

28. The injection device according to claim 21, wherein the shuttle member is further arranged to cooperate with the needle shield to release the needle shield.

29. The injection device according to claim 28, wherein the operating member is coupled to the shuttle member such that movement of the operating member from the first position to an intermediate position causes movement of the shuttle member in the distal direction to cooperate with the needle shield.

30. The injection device according to claim 1, wherein the operating member is arranged to cooperate with the container body to move the container body in the proximal direction.

31. The injection device according to claim 30, comprising an inclined formation arranged to move the operating member in the proximal direction upon turning movement of the operating member.

32. The injection device according to claim 30, comprising a first inclined formation arranged to move the operating member in the distal direction upon turning movement of the operating member from the first position to an intermediate position to release the needle shield and a second inclined formation arranged to move the operating member in the proximal direction upon turning movement of the operating member from the intermediate position to the second position to move the container body in the proximal direction.

33. The injection device according to claim 1, comprising guide means for guiding movement of the operating member between the first position and the second position.

34. The injection device according to claim 33, wherein the guide means comprises the inclined formation or at least one of the inclined formations.

35. The injection device according to claim 1, comprising a drive mechanism arranged to hold the plunger in a starting position and to drive the plunger in a distal direction with respect to the housing to expel medicament from the container upon activation of the drive mechanism.

36. The injection device according to claim 1, wherein the priming mechanism is arranged to push the stopper of the container against a priming member upon movement of the operating member from the first position to the second position.

37. The injection device according to claim 36, wherein the priming member comprises the plunger.

38. The injection device according to claim 36, wherein the plunger is movable with respect to the priming member.

39. The injection device according to claim 38, wherein the plunger comprises a bore, and wherein the priming member comprises a rod received in the bore.

40. The injection device according to claim 38, wherein a distal end of the priming member is disposed distally with respect to the plunger when the plunger is in its starting position.

41. The injection device according to claim 38, wherein the priming member is attached to the housing.

42. The injection device according to claim 41, wherein the priming member is detachable from the housing upon movement of the plunger in the distal direction.

43. The injection device according to claim 42, wherein the plunger is arranged to carry the priming member in the distal direction upon movement of the plunger in the distal direction.

44. The injection device according to claim 1, comprising a container guide for receiving the container body.

45. The injection device according to claim 44, wherein the container guide is movable with respect to the housing between a retracted position and an advanced position in which the container is positioned for injection of medicament.

46. The injection device according to claim 1, wherein the plunger is adjustable in length.

47. The injection device according to claim 1, further comprising the pre-filled container, the pre-filled container comprising;
a syringe having a syringe body for containing the medicament;
the needle being disposed at a distal end of the syringe body;
the removable needle shield; and
the stopper for expelling medicament through the needle.

* * * * *

UNITED STATES PATENT AND TRADEMARK OFFICE
CERTIFICATE OF CORRECTION

PATENT NO.       : 10,512,729 B2
APPLICATION NO.  : 15/749582
DATED            : December 24, 2019
INVENTOR(S)      : Grimoldby et al.

Page 1 of 1

It is certified that error appears in the above-identified patent and that said Letters Patent is hereby corrected as shown below:

In the Claims

In Column 28, Line 53 (Claim 28), delete "release the needle shield." and substitute therefor --release the needle shield from the needle.--.

Signed and Sealed this
Eighth Day of September, 2020

Andrei Iancu
*Director of the United States Patent and Trademark Office*